US009206400B2

(12) United States Patent
Roy et al.

(10) Patent No.: US 9,206,400 B2
(45) Date of Patent: Dec. 8, 2015

(54) SALINITY TOLERANCE IN PLANTS

(75) Inventors: Stuart John Roy, South Australia (AU); Mark Alfred Tester, Toorak Gardens (AU)

(73) Assignee: Australian Centre for Plant Functional Genomics Pty, Ltd, Glen Osmond (AU)

( * ) Notice: Subject to any disclaimer, the term of this patent is extended or adjusted under 35 U.S.C. 154(b) by 575 days.

(21) Appl. No.: 13/062,190

(22) PCT Filed: Sep. 4, 2009

(86) PCT No.: PCT/AU2009/001154
§ 371 (c)(1),
(2), (4) Date: May 9, 2011

(87) PCT Pub. No.: WO2010/025513
PCT Pub. Date: Mar. 11, 2010

(65) Prior Publication Data
US 2011/0209243 A1   Aug. 25, 2011

(30) Foreign Application Priority Data

Sep. 4, 2008   (AU) ................................ 2008904596

(51) Int. Cl.
*C12N 15/82* (2006.01)
*C12N 9/12* (2006.01)
*C07K 14/415* (2006.01)

(52) U.S. Cl.
CPC ................ *C12N 9/12* (2013.01); *C07K 14/415* (2013.01); *C12N 15/8273* (2013.01)

(58) Field of Classification Search
None
See application file for complete search history.

(56) References Cited

U.S. PATENT DOCUMENTS

| 2002/0083485 | A1 | 6/2002 | Zhu et al. | |
|---|---|---|---|---|
| 2006/0123505 | A1* | 6/2006 | Kikuchi et al. | 800/278 |
| 2006/0150283 | A1* | 7/2006 | Alexandrov et al. | 800/288 |
| 2007/0294782 | A1* | 12/2007 | Abad et al. | 800/278 |

FOREIGN PATENT DOCUMENTS

WO   WO 2006/079045 A2   7/2006

OTHER PUBLICATIONS

GenBank Accession No. Q6ERS4. CBL-interacting protein kinase 16 (OsCIPK16). Published Jul. 1, 2008. pp. 1-3.*
Xiang et al. Characterization of stress-responsive CIPK genes in rice for stress tolerance improvement. Plant Physiology. 2007. 144: 1416-1428.*
Halford et al. Metabolic signalling and carbon partitioning: role of Snf1-related (SnRK1) protein kinase. Journal of Experimental Botany. 2003. 54(382): 467-475.*
GenBank Accession No. Q9SEZ7. CBL-interacting serine/threonine-protein kinase 16. Published Feb. 19, 2014. pp. 1-6.*
GenBank Accession No. P92937. CBL-interacting serine/threonine-protein kinase 15. Published Feb. 19, 2014. pp. 1-8.*
GenBank Accession No. Q6ERS4. CBL-interacting protein kinase 16. Published Dec. 11, 2013. pp. 1-6.*
Zhu. Salt and drought stress signal transfuction in plants. Annual Reviews in Plant Biology. 2002. 53: 247-273.*
Tripathi, V., et al., "CIPK6, a CBL-interacting protein kinase is required for development and salt tolerance in plants," *The Plant Journal*, vol. 58, pp. 778-790 (2009).
Xiang, Y., et al., "Characterization of Stress-Responsive *CIPK* Genes in Rice for Stress Tolerance Improvement," *Plant Physiology*, vol. 144, pp. 1416-1428 (Jul. 2007).
Zhao, J., et al., "Cloning and characterization of a novel CBL-interacting protein kinase from maize," *Plant Molecular Biology*, vol. 69, pp. 661-674 (2009).
Gao, et al. "Molecular characterization of functional domains in the protein kinase SOS2 that is required for plant salt tolerance," *The Plant Cell* 13 (2001): pp. 1383-1400.
Kolukisaoglu, et al. "Calcium sensors and their interacting protein kinases: genomics of the Arabidopsis and rice CBL-CIPK signaling networks," *Plant Physiology* 134 (2004): pp. 43-58.
Batistic & Kudla, "Integration and channeling of calcium signaling through the CBL calcium sensor/ CIPK protein kinase network," *Planta* 219:915-924, 2004.
Munns & Tester, "Mechanisms of Salinity Tolerance," *Annu. Rev. Plant Biol.* 59:651-681, 2008.

* cited by examiner

*Primary Examiner* — Anne Kubelik
*Assistant Examiner* — Ashley K Buran
(74) *Attorney, Agent, or Firm* — Klarquist Sparkman, LLP

(57) ABSTRACT

The present invention is predicated, in part, on the identification of a gene involved in salinity tolerance in plants. As such, the present invention relates to methods for modulating salinity tolerance in plants. The present invention also provides plant cells and plants having modulated salinity tolerance. In further embodiments, the present invention also provides methods for determining the salinity tolerance of plant cells and plants.

8 Claims, 15 Drawing Sheets

SALINITY TOLERANCE IN PLANTS

PRIORITY CLAIM

This patent application is a U.S. National Stage Application of PCT/AU2009/001154, filed Sep. 4, 2009, which claims priority to Australian provisional patent application 2008904596 filed 4 Sep. 2008, the entire contents of which are incorporated by reference herein in their entirety.

FIELD

The present invention is predicated, in part, on the identification of a gene involved in salinity tolerance in plants. As such, the present invention relates to methods for modulating salinity tolerance in plants. The present invention also provides plant cells and plants having modulated salinity tolerance. In further embodiments, the present invention also provides methods for determining the salinity tolerance of plant cells and plants.

BACKGROUND

Salinity is a major abiotic stress affecting crop plants in Australia, resulting in substantial loss of yield and millions of dollars of lost revenue. High levels of $Na^+$ in shoot tissue have adverse osmotic effects and reduce the amount of $K^+$ available for essential biological processes. Crucially, yield in cereals is commonly inversely proportional to the extent of shoot $Na^+$ accumulation.

In order to combat this problem it would be desirable to understand how salt gets into a plant and how a plant deals with it once it is inside. Therefore, there is a need to identify the genes, resistant plant cultivars and cellular processes that are involved in salt tolerance with the goal of introducing these factors into commercially available crops.

Reference to any prior art in this specification is not, and should not be taken as, an acknowledgment or any form of suggestion that this prior art forms part of the common general knowledge in any country.

SUMMARY

The present invention is predicated, in part, on the use of recombinant inbred lines (RILs) of *Arabidopsis thaliana* to identify quantitative trait loci (QTLs) linked to novel genes involved in $Na^+$ exclusion. A Bay-0×Shahdara mapping population, produced from two parents with large geographical, ecological and genetic distances, has been used to identify a novel, significant QTL linked to $Na^+$ exclusion from the shoot, located on chromosome 2. Those RILs with the Bay-0 genotype at the QTL have a two-fold reduction in $Na^+$ accumulation when compared to those with the Shandara genotype. By creating 20 cleaved amplified polymorphic sequence (CAPS) markers to fine map the QTL a candidate gene of interest, CIPK16, was identified.

In a first aspect, the present invention provides a method for modulating the salinity tolerance of a plant cell, the method comprising modulating the expression of a CIPK16 polypeptide in the plant cell.

In some embodiments, the expression of the CIPK16 polypeptide is modulated by modulating the expression of a CIPK16 nucleic acid in the plant cell.

In some embodiments, expression of the CIPK16 polypeptide and/or CIPK26 nucleic acid is upregulated in the plant cell and the salinity tolerance of the plant cell is increased. In some embodiments expression of the CIPK16 polypeptide and/or CIPK16 nucleic acid is downregulated in the plant cell and the salinity tolerance of the plant cell is decreased.

In a second aspect, the present invention provides a method for modulating the salinity tolerance of a multicellular structure comprising a plurality of plant cells, the method comprising modulating the salinity tolerance of one or more plant cells in the multicellular structure according to the method of the first aspect of the invention.

In some embodiments, expression of a CIPK16 polypeptide and/or CIPK16 nucleic acid is upregulated in the one or more plant cells and the salinity tolerance of the multicellular structure is increased. In some embodiments, expression of a CIPK16 polypeptide and/or CIPK16 nucleic acid is downregulated in the one or more plant cells and the salinity tolerance of the multicellular structure is decreased.

In some embodiments, the multicellular structure comprises a whole plant, plant tissue, plant organ, plant part, plant reproductive material or cultured plant tissue.

In a third aspect, the present invention provides a genetically modified plant cell having modulated salinity tolerance relative to a wild type form of the plant cell, wherein the expression of a CIPK16 polypeptide and/or a CIPK76 nucleic acid is modulated in the plant cell.

In some embodiments, expression of the CIPK16 polypeptide and/or CIPK16 nucleic acid is upregulated in the plant cell and the salinity tolerance of the plant cell is increased. In some embodiments, expression of the CIPK16 polypeptide and/or CIPK16 nucleic acid is downregulated in the plant cell and the salinity tolerance of the plant cell is decreased.

In a fourth aspect, the present invention provides a multicellular structure having modulated salinity tolerance, wherein the multicellular structure comprises one or more plant cells according to the third aspect of the invention.

In some embodiments, expression of a CIPK16 polypeptide and/or CIPK16 nucleic acid is upregulated in the one or more plant cells and the salinity tolerance of the multicellular structure is increased. In some embodiments, expression of a CIPK16 polypeptide and/or CIPK16 nucleic acid is downregulated in the one or more plant cells and the salinity tolerance of the multicellular structure is decreased.

In some embodiments, the multicellular structure comprises a whole plant, plant tissue, plant organ, plant part, plant reproductive material or cultured plant tissue.

In a fifth aspect, the present invention provides a method for ascertaining or predicting the salinity tolerance of a plant cell, the method comprising determining the expression of a CIPK16 polypeptide and/or a CIPK16 nucleic acid in the plant cell.

In some embodiments, relatively high expression of a CIPK16 polypeptide and/or CIPK16 nucleic acid in the plant cell is associated with increased salinity tolerance in the plant cell. In some embodiments, relatively low expression of a CIPK16 polypeptide and/or CIPK16 nucleic acid in the plant cell is associated with decreased salinity tolerance in the plant cell.

In a sixth aspect, the present invention provides a method for ascertaining or predicting the salinity tolerance of a multicellular structure comprising a plant cell, the method comprising ascertaining or predicting the salinity tolerance of a plant cell in the multicellular structure according to the method of the fifth aspect of the invention.

In some embodiments, relatively high expression of a CIPK16 polypeptide and/or CIPK16 nucleic acid in the plant cell is associated with increased salinity tolerance in the multicellular structure. In some embodiments, relatively low expression of a CIPK16 polypeptide and/or CIPK16 nucleic acid in the plant cell is associated with decreased salinity tolerance in the multicellular structure.

In some embodiments, the multicellular structure comprises a whole plant, plant tissue, plant organ, plant part, plant reproductive material or cultured plant tissue.

Nucleotide and amino acid sequences are referred to herein by a sequence identifier number (SEQ ID NO:). The SEQ ID NOs: correspond numerically to the sequence identifiers <400> 1 (SEQ ID NO:1), <400> 2 (SEQ ID NO:2), etc. A summary of the sequence identifiers is provided in Table 1. The Sequence Listing is submitted as an ASCII compliant text file named "Sequence_Listing.txt", created on Aug. 14, 2014, and having a size of 16 kilobytes, which is incorporated by reference herein.

TABLE 1

Summary of Sequence Identifiers

| Sequence Identifier | Sequence |
|---|---|
| SEQ ID NO: 1 | Arabidopsis thaliana ecotype Bay-0 CIPK16 promoter nucleotide sequence |
| SEQ ID NO: 2 | AtCIPK16 forward primer nucleotide sequence |
| SEQ ID NO: 3 | AtCIPK16 reverse primer nucleotide sequence |
| SEQ ID NO: 4 | AtCyclophilin forward primer nucleotide sequence |
| SEQ ID NO: 5 | AtCyclophilin reverse primer nucleotide sequence |
| SEQ ID NO: 6 | AtTUA2 forward primer nucleotide sequence |
| SEQ ID NO: 7 | AtTUA2 reverse primer nucleotide sequence |
| SEQ ID NO: 8 | AtGAPA forward primer nucleotide sequence |
| SEQ ID NO: 9 | AtGAPA reverse primer nucleotide sequence |
| SEQ ID NO: 10 | AtCIPK16 whole gene forward primer nucleotide sequence |
| SEQ ID NO: 11 | AtCIPK16 whole gene reverse primer nucleotide sequence |
| SEQ ID NO: 12 | amiRNA AtCIPK16-1 nucleotide sequence |
| SEQ ID NO: 13 | amiRNA AtCIPK16-2 nucleotide sequence |
| SEQ ID NO: 14 | I miR-s primer nucleotide sequence |
| SEQ ID NO: 15 | IImiR-a primer nucleotide sequence |
| SEQ ID NO: 16 | III miR*s primer nucleotide sequence |
| SEQ ID NO: 17 | IV miR*a primer nucleotide sequence |
| SEQ ID NO: 18 | I miR-s primer nucleotide sequence |
| SEQ ID NO: 19 | IImiR-a primer nucleotide sequence |
| SEQ ID NO: 20 | III miR*s primer nucleotide sequence |
| SEQ ID NO: 21 | IV miR*a primer nucleotide sequence |
| SEQ ID NO: 22 | MIR319a primer A nucleotide sequence |
| SEQ ID NO: 23 | MIR319a primer B nucleotide sequence |
| SEQ ID NO: 24 | AtCIPK16 forward primer nucleotide sequence |
| SEQ ID NO: 25 | AtCIPK16 reverse primer nucleotide sequence |
| SEQ ID NO: 26 | Hygromycin forward primer nucleotide sequence |
| SEQ ID NO: 27 | Hygromycin forward primer nucleotide sequence |
| SEQ ID NO: 28 | Basta forward primer nucleotide sequence |
| SEQ ID NO: 29 | Basta reverse primer nucleotide sequence |
| SEQ ID NO: 30 | AtACT2 forward primer nucleotide sequence |
| SEQ ID NO: 31 | AtACT2 reverse primer nucleotide sequence |
| SEQ ID NO: 32 | OsGAP forward primer nucleotide sequence |
| SEQ ID NO: 33 | OsGAP reverse primer nucleotide sequence |

DESCRIPTION OF EXEMPLARY EMBODIMENTS

It is to be understood that the following description is for the purpose of describing particular embodiments only and is not intended to be limiting with respect to the above description.

In a first aspect, the present invention provides a method for modulating the salinity tolerance of a plant cell, the method comprising modulating the expression of a CIPK16 polypeptide in the plant cell.

The plant cells contemplated by the present invention may include any plant cell including angiosperm or gymnosperm higher plant cells as well as lower plant cells such as bryophyte, fern and horsetail cells.

In some embodiments, the plant cell may be a monocotyledonous angiosperm plant cell.

In some embodiments, the monocotyledonous plant cell may be a cereal crop plant cell. As used herein, the term "cereal crop plant" includes members of the Poaceae (grass family) that produce edible grain for human or animal food. Examples of Poaceae cereal crop plants which in no way limit the present invention include barley, wheat, rice, maize, millets, sorghum, rye, triticale, oats, teff, wild rice, spelt and the like. However, the term cereal crop plant should also be understood to include a number of non-Poaceae species that also produce edible grain and are known as the pseudocereals, such as amaranth, buckwheat and quinoa.

In some embodiments, the plant cell may be a rice plant cell. As referred to herein, "rice" includes several members of the genus Oryza including the species Oryza sativa and Oryza glaberrima. The term "rice" thus encompasses rice cultivars such as japonica or sinica varieties, indica varieties and javonica varieties. In some embodiments, the term "rice" refers to rice of the species Oryza sativa.

In some embodiments, the plant cell may be a dicotyledonous angiosperm plant cell. Exemplary divots include, for example, Arabidopsis spp., Medicago spp, Nicotiana spp., soybean, canola, oil seed rape, sugar beet, mustard, sunflower, tomato, potato, safflower, cassava, yams, sweet potato, other Brassicaceae such as Thellungiella halophila, among others.

As set out above, the present invention contemplates modulating the salinity tolerance of a plant cell.

The term "salinity" as used herein generally refers to the level of all salts in the growing environment of a plant. Thus, in some embodiments, the term "salinity tolerance" relates to the capacity of a plant cell or plant to survive and/or grow at a particular environmental salt concentration.

However, the most relevant salt for a majority of cropping systems is NaCl. Thus, in some embodiments, the term "salinity tolerance" refers to the capacity of a plant to survive and/or grow at a particular environmental sodium concentration. In some embodiments, salinity tolerance also refers to the ability of a plant to maintain a suitable sodium concentration in one or more tissues of the plant (eg. the shoots) at a particular environmental sodium concentration.

"Modulation" of salinity tolerance refers to an increase or decrease in the salinity tolerance of a plant cell or plant relative to an unmodified or wild type form of the cell.

An increase in salinity tolerance may include, for example:
- an increase (relative to an unmodified or wild type form of the plant) in the environmental salinity level at which a plant cell or plant may survive, grow or maintain a suitable shoot sodium concentration;
- an increase (relative to an unmodified or wild type form of the plant) in the biomass production, growth rate, seed yield or the like of a plant at a particular level of environmental salinity; and/or
- a decrease (relative to an unmodified or wild type form of the plant) in the rate or level of sodium accumulation in the plant or a particular part thereof (such as the shoots) at a particular environmental salinity level.

Conversely, a decrease in salinity tolerance may include, for example:
- a decrease (relative to an unmodified or wild type form of the plant) in the environmental salinity level at which a plant cell or plant may survive, grow or maintain a suitable shoot sodium concentration;

a decrease (relative to an unmodified or wild type form of the plant) in the biomass production, growth rate, seed yield or the like of a plant at a particular level of environmental salinity; and/or an increase (relative to an unmodified or wild type form of the plant) in the rate or level of sodium accumulation in the plant or a particular part thereof (such as the shoots) at a particular environmental salinity level.

As set out above, the present invention contemplates modulating the salinity tolerance of a plant cell by modulating the expression of a CIPK16 polypeptide in the plant cell.

As referred to herein, a "CIPK16 polypeptide" includes the *Arabidopsis thaliana* polypeptide described under TAIR accession number At2g25090. The term "CIPK16 polypeptide" should also be understood extend to functional homologs of the polypeptide described under TAIR accession number At2g25090.

"Functional homologs" of a polypeptide described under TAIR accession number At2g25090 should be understood to include polypeptides which modulate the salinity tolerance of a plant. In some embodiments a functional homolog may comprise, for example, a polypeptide which has one or more amino acid insertions, deletions or substitutions relative to the polypeptide comprising the amino acid sequence set forth in At2g25090; a mutant form or allelic variant of the polypeptide comprising the amino acid sequence set forth in At2g25090; an ortholog of the polypeptide comprising the amino acid sequence set forth in At2g25090 in another plant species and the like.

In some embodiments, a functional homolog of a polypeptide comprising the amino acid sequence set forth in At2g25090 also comprises at least 40%, 42%, 44%, 46%, 48%, 50% 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98% or 100% amino acid sequence identity to At2g25090.

When comparing amino acid sequences, the compared sequences should be compared over a comparison window of at least 100 amino acid residues, at least 200 amino acid residues, at least 300 amino acid residues, at least 400 amino acid residues or over the full length of SEQ ID NO: 2. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerized implementations of algorithms such the BLAST family of programs as, for example, disclosed by Altschul et (*Nucl. Acids Res.* 25: 3389-3402, 1997). A detailed discussion of sequence analysis can be found in Unit 19, 3 of Ausubel et al. (*Current Protocols in Molecular Biology*, John Wiley & Sons Inc, 1998).

As a result of inconsistent nomenclature of genes and proteins within the CIPK family, it should be understood that orthologs of *Arabidopsis thaliana* CIPK16 (At2g25090) may be classified into different CIPK subfamilies. For example, homologs or orthologs of *Arabidopsis thaliana* CIPK16 (At2g25090) may include *Arabidopsis thaliana* CIPK5 (At5g10930), *Arabidopsis thaliana* CIPK25 (At5g25110), *Oryza sativa* CIPK16 (Q6ERS4), *Porulus trichocarpa* CIPK20 (ABJ91235), *Populus trichocarpa* CIPK23 (ABJ91229) and *Populus trichocarpa* CIPK6 (ABJ91234).

As set out above, the present invention is predicated, in part, on modulating the expression of a CIPK16 polypeptide in a cell.

As referred to herein, modulation of the "expression" of a CIPK16 polypeptide includes modulating the level and/or activity of the polypeptide.

Modulation of the "level" of the polypeptide should be understood to include an increase or decrease in the level or amount of a CIPK16 polypeptide in a cell or a particular part of a cell. Similarly, modulation of the "activity" of a CIPK16 polypeptide should be understood to include an increase or decrease in, for example, the total activity, specific activity, half-life and/or stability of a CIPK16 polypeptide in the cell.

By "increasing" is intended, for example, a 1%, 5%, 10%, 20%, 30%, 40%, 50%, 60%, 70%, 80%, 90%, 100%, 2-fold, 5-fold, 10-fold, 20 fold, 50-fold, 100-fold increase in the level of activity of a CIPK16 polypeptide in the cell. By "decreasing" is intended, for example, a 1%, 5%, 10%, 20%, 30%, 40%, 50%, 60%, 70%, 80%, 90%, 91%, 92%, 93%, 94%, 95%, 96%, 97%, 98%, 99%, 100% reduction in the level or activity of a CIPK16 polypeptide in the cell.

"Modulating" should also be understood to include introducing a particular CIPK16 polypeptide into a cell which does not normally express the introduced polypeptide, or the substantially complete inhibition of a CIPK16 polypeptide activity in a cell that normally expresses such a polypeptide.

In some embodiments, the expression of a CIPK16 polypeptide is upregulated in the plant cell. "Upregulation" should be understood to include an increase in the level or activity of a CIPK16 in a cell and/or introducing a particular CIPK16 polypeptide into a cell which does not normally express the introduced polypeptide.

In some embodiments, increasing or upregulating the expression of a CIPK16 polypeptide in a cell effects an increase in the salinity tolerance of the cell.

In another embodiment, the expression of a CIPK16 polypeptide is downregulated in the plant cell. "Downregulation" should be understood to include a decrease in the level or activity of a CIPK16 in a cell and/or substantially complete inhibition of a particular CIPK16 polypeptide in a cell which normally expresses the CIPK16 polypeptide.

In some embodiments, decreasing or downregulating the expression of a CIPK16 polypeptide in a cell effects a decrease in the salinity tolerance of the cell.

The present invention contemplates any means by which the expression of a CIPK16 polypeptide in a cell may be modulated. This includes, for example, methods such as the application of agents which modulate CIPK16 polypeptide activity in a cell, including the application of agonists or antagonists; the application of agents which mimic CIPK16 polypeptide activity in a cell; modulating the expression of a nucleic acid which encodes a CIPK16 polypeptide in the cell; effecting the expression of an altered or mutated nucleic acid in a cell such that a CIPK16 polypeptide with increased or decreased specific activity, half-life and/or stability is expressed by the cell; or modulating the expression level, pattern and/or targeting of a CIPK16 polypeptide in a cell for example via modification of a transcriptional control sequence and/or signal polypeptide associated with the CIPK16 polypeptide.

In some embodiments, the expression of the polypeptide is modulated by modulating the expression of a nucleic acid which encodes a CIPK16 polypeptide in the cell.

As referred to herein, a nucleic acid which encodes a CIPK16 polypeptide ("CIPK16 nucleic acid") refers to any nucleic acid which encodes a CIPK16 polypeptide as hereinbefore described.

The CIPK16 nucleic acids contemplated by the present invention may be derived from any source. For example, the CIPK16 nucleic acids may be derived from an organism, such as a plant. Alternatively, the CIPK16 nucleic acid may be a synthetic nucleic acid.

The CIPK16 nucleic acids contemplated by the present invention may also comprise one or more non-translated regions such as 3' and 5' untranslated regions and/or introns.

The CIPK16 nucleic acids contemplated by the present invention may comprise, for example, mRNA sequences, cDNA sequences or genomic nucleotide sequences.

The term "modulating" with regard to the expression of a CIPK16 nucleic acid may include increasing or decreasing the transcription and/or translation of a CIPK16 nucleic acid in a cell.

By "increasing" is intended, for example a 1%, 5%, 10%, 20%, 30%, 40%, 50%, 60%, 70%, 80%, 90%, 100%, 2-fold, 5-fold, 10-fold, 20-fold, 50-fold, 100-fold or greater increase in the transcription and/or translation of a CIPK16 nucleic acid. By "decreasing" is intended, for example, a 1%, 5%, 10%, 20%, 30%, 40%, 50%, 60%, 70%, 80%, 90%, 91%, 92%, 93%, 94%, 95%, 96%, 97%, 98%, 99%, 100% reduction in the transcription and/or translation of a CIPK16 nucleic acid. Modulating also comprises introducing expression of a CIPK16 nucleic acid not normally found in a particular cell; or the substantially complete inhibition (eg. knockout) of expression of a CIPK16 nucleic acid in a cell that normally has such activity.

In some embodiments, the expression of a CIPK16 nucleic acid is upregulated in the plant cell. "Upregulation" should be understood to include an increase in the transcription and/or translation of a CIPK16 nucleic acid in a cell and/or introducing transcription and/or translation of a particular CIPK16 nucleic acid in a cell which does not normally express the introduced nucleic acid.

In some embodiments, the expression of a CIPK16 nucleic acid is downregulated in the plant cell. "Downregulation" should be understood to include a decrease in the transcription and/or translation of a CIPK16 nucleic acid in a cell and/or substantially eliminating transcription and/or translation of a particular CIPK16 nucleic acid in a cell which does not normally expresses the CIPK16 nucleic acid.

The present invention contemplates any means by which the expression of a CIPK16 nucleic acid may be modulated. Methods for modulating the expression of a CIPK16 nucleic acid include, for example: genetic modification of the cell to upregulate or downregulate endogenous CIPK16 nucleic acid expression; genetic modification by transformation with a CIPK16 nucleic acid; genetic modification to increase the copy number of a CIPK16 nucleic acid in the cell; administration of a nucleic acid molecule to the cell which modulates expression of an endogenous CIPK16 nucleic acid in the cell; and the like.

In some embodiments, the expression of a CIPK16 nucleic acid is modulated by genetic modification of the cell. The term "genetically modified", as used herein, should be understood to include any genetic modification that effects an alteration in the expression of a CIPK16 nucleic acid in the genetically modified cell relative to a non-genetically modified form of the cell. Exemplary types of genetic modification include: random mutagenesis such as transposon, chemical, UV and phage mutagenesis together with selection of mutants which overexpress or underexpress an endogenous CIPK16 nucleic acid; transient or stable introduction of one or more nucleic acid molecules into a cell which direct the expression and/or overexpression of CIPK16 nucleic acid in the cell; modulation of an endogenous CIPK16 polypeptide by site-directed mutagenesis of an endogenous CIPK16 nucleic acid; introduction of one or more nucleic acid molecules which inhibit the expression of an endogenous CIPK16 nucleic acid in the cell, eg. a cosuppression construct, an RNAi construct or a miRNA construct; and the like.

In some embodiments, the present invention contemplates increasing the level of a CIPK16 polypeptide in a cell, by introducing the expression of a CIPK16 nucleic acid into the cell, upregulating the expression of a CIPK16 nucleic acid in the cell and/or increasing the copy number of a CIPK16 nucleic acid in the cell.

Methods for transformation and expression of an introduced nucleotide sequence in various cell types are well known in the art, and the present invention contemplates the use of any suitable method.

However, by way of example with regard to the transformation of plant cells, reference is made to Zhao et al. (*Mol Breeding* DOI 10.1007/s11032-006-9005-6, 2006), Katsuhara et al. (*Plant Cell Physiol* 44(12): 1378-4383, 2003), Ohta et al. (*FEBS Letters* 532: 279-282, 2002) and Wu et al. (*Plant Science* 169: 65-73, 2005). Further suitable methods for introduction of a nucleic acid molecule into plant cells include, for example: *Agrobacterium*-mediated transformation, other bacterially-mediated transformation (see Broothaerts et al., 2005, supra) microprojectile bombardment based transformation methods and direct DNA uptake based methods. Roa-Rodriguez et al. (*Agrobacterium-mediated transformation of plants*, 3$^{rd}$ Ed, CAMBIA Intellectual Property Resource, Canberra, Australia, 2003) review a wide array of suitable *Agrobacterium*-mediated plant transformation methods for a wide range of plant species. Microprojectile bombardment may also be used to transform plant tissue and methods for the transformation of plants, particularly cereal plants, and such methods are reviewed by Casas et al. (*Plant Breeding Rev.* 13: 235-264, 1995). Direct DNA uptake transformation protocols such as protoplast transformation and electroporation are described in detail in Galbraith et al. (eds.), *Methods in Cell Biology* Vol. 50, Academic Press, San Diego, 1995). In addition to the methods mentioned above, a range of other transformation protocols may also be used. These include infiltration, electroporation of cells and tissues, electroporation of embryos, microinjection, pollen-tube pathway, silicon carbide- and liposome mediated transformation. Methods such as these are reviewed by Rakoczy-Trojanowska (*Cell. Mol. Biol. Lett.* 7: 849-858, 2002). A range of other plant transformation methods may also be evident to those of skill in the art.

In further embodiments the present invention also provides methods for downregulating expression of a CIPK16 nucleic acid in a cell. For example, with the identification of CIPK16 nucleic acid sequences, the present invention also facilitates methods such as knockout, knockdown or downregulation of a CIPK16 nucleic acid in a cell using methods including, for example:

insertional mutagenesis including knockout or knockdown of a nucleic acid in a cell by homologous recombination with a knockout construct (for an example of targeted gene disruption see Terada et al., *Nat. Biotechnol.* 20: 1030-1034, 2002);

post-transcriptional gene silencing (PTGS) or RNAi of a nucleic acid in a cell (for review of PTGS and RNAi see Sharp, *Genes Dev.* 15(5): 485-490, 2001; and Hannon, *Nature* 418: 244-51, 2002);

transformation of a cell with an antisense construct directed against a nucleic acid (for examples of antisense suppression see van der Krol et al., *Nature* 333: 866-869; van der Krol et al., *BioTechniques* 6: 958-967; and van der Krol et al., *Gen. Genet.* 220: 204-212);

transformation of a cell with a co-suppression construct directed against a nucleic acid (for an example of co-suppression see van der Krol et al., *Plant Cell* 2(4); 291-299);

transformation of a cell with a construct encoding a double stranded RNA directed against a nucleic acid (for an example of dsRNA mediated gene silencing see Waterhouse et al., *Proc. Natl. Acad. Sci. USA* 95; 13959-13964, 1998);

transformation of a cell with a construct encoding an siRNA or hairpin RNA directed against a nucleic acid (for an example of siRNA or hairpin RNA mediated gene silencing see Lu et al., *Nucl. Acids Res.* 32(21); e171; doi:10.1093/nar/gnh170, 2004); and insertion of a miRNA target sequence such that it is in operable connection with a nucleic acid (for an example of miRNA mediated gene silencing see Brown et al., *Blood* 110(13): 4144-4152, 20077.

The present invention also facilitates the downregulation of a CIPK16 nucleic acid in a cell via the use of synthetic oligonucleotides, for example, siRNAs or miRNAs directed against a CIPK16 nucleic acid (for examples of synthetic siRNA mediated silencing see Caplen et al., *Proc. Natl. Acad. Sci. USA* 98: 9742-9747, 2001; Elbashir et al., *Genes Dev.* 15: 188-200, 2001; Elbashir et al., *Nature* 411: 494-498, 2001; Elbashir et al., *EMBO J.* 20: 6877-6888, 2001; and Elbashir et al., *Methods* 26: 199-213, 2002).

In addition to the examples above, the introduced nucleic acid may also comprise a nucleotide sequence which is not directly related to a CIPK16 nucleic acid but, nonetheless, may directly or indirectly modulate the expression of a CIPK16 nucleic acid in a cell. Examples include nucleic acid molecules that encode transcription factors or other proteins which promote or suppress the expression of an endogenous CIPK16 nucleic acid molecule in a cell; and other non-translated RNAs which directly or indirectly promote or suppress endogenous CIPK16 polypeptide expression and the like.

In order to effect expression of an introduced nucleic acid in a cell, where appropriate, the introduced nucleic acid may be operably connected to one or more transcriptional control sequences and/or promoters.

The term "transcriptional control sequence" should be understood to include any nucleic acid sequence which effects the transcription of an operably connected nucleic acid. A transcriptional control sequence may include, for example, a leader, polyadenylation sequence, promoter, enhancer or upstream activating sequence, and transcription terminator. Typically, a transcriptional control sequence at least includes a promoter. The term "promoter" as used herein, describes any nucleic acid which confers, activates or enhances expression of a nucleic acid molecule in a cell.

In some embodiments, at least one transcriptional control sequence is operably connected to a CIPK16 nucleic acid. For the purposes of the present specification, a transcriptional control sequence is regarded as "operably connected" to a given gene or other nucleotide sequence when the transcriptional control sequence is able to promote, inhibit or otherwise modulate the transcription of the gene or other nucleotide sequence.

A promoter may regulate the expression of an operably connected nucleotide sequence constitutively, or differentially, with respect to the cell, tissue, organ or developmental stage at which expression occurs, in response to external stimuli such as physiological stresses, pathogens, or metal ions, amongst others, or in response to one or more transcriptional activators. As such, the promoter used in accordance with the methods of the present invention may include, for example, a constitutive promoter, an inducible promoter, a tissue-specific promoter or an activatable promoter.

Plant constitutive promoters typically direct expression in nearly all tissues of a plant and are largely independent of environmental and developmental factors. Examples of constitutive promoters that may be used in accordance with the present invention include plant viral derived promoters such as the Cauliflower Mosaic Virus 35S and 19S (CaMV 35S and CaMV 19S) promoters; bacterial plant pathogen derived promoters such as opine promoters derived from *Agrobacterium* spp., eg. the *Agrobacterium*-derived nopaline synthase (nos) promoter; and plant-derived promoters such as the rubisco small subunit gene (rbcS) promoter, the plant ubiquitin promoter (Pubi) and the rice actin promoter (Pact).

In some embodiments, a constitutive transcriptional control sequence may be used. In some embodiments, the constitutive transcriptional control sequence comprises one or more repeats of a CaMV 35S promoter. In some embodiments the transcriptional control sequence comprises two repeats of the CaMV 35S promoter.

"Inducible" promoters include, but are not limited to, chemically inducible promoters and physically inducible promoters. Chemically inducible promoters include promoters which have activity that is regulated by chemical compounds such as alcohols, antibiotics, steroids, metal ions or other compounds. Examples of chemically inducible promoters include: alcohol regulated promoters (eg. see European Patent 637 339); tetracycline regulated promoters (eg. see U.S. Pat. No. 5,851,796 and U.S. Pat. No. 5,464,758); steroid responsive promoters such as glucocorticoid receptor promoters (eg. see U.S. Pat. No. 5,512,483), estrogen receptor promoters (eg. see European Patent Application 1 232 273), ecdysone receptor promoters (eg. see U.S. Pat. No. 6,379,945) and the like; metal-responsive promoters such as metallothionein promoters (eg. see U.S. Pat. No. 4,940,661, U.S. Pat. No. 4,579,821 and U.S. Pat. No. 4,601,978); and pathogenesis related promoters such as chitinase or lysozyme promoters (eg. see U.S. Pat. No. 5,654,414) or PR protein promoters (eg. see U.S. Pat. No. 5,689,044, U.S. Pat. No. 5,789,214, Australian Patent 708850, U.S. Pat. No. 6,429,362).

In some embodiments, a salt or sodium inducible promoter may be used. Examples of such promoters include the AtGRP9 promoter (Chen et al., *Journal of Plant Research* 120: 337-343, 2007; accession number At2g05440) and the VHAc3 promoter (accession number At4g38920).

An inducible promoter may also be a physically regulated promoter which is regulated by non-chemical environmental factors such as temperature (both heat and cold), light and the like. Examples of physically regulated promoters include heat shock promoters (eg. see U.S. Pat. No. 5,447,858, Australian Patent 732872, Canadian Patent Application 1324097); cold inducible promoters (eg. see U.S. Pat. No. 6,479,260, U.S. Pat. No. 6,184,443 and U.S. Pat. No. 5,847,102); light inducible promoters (eg. see U.S. Pat. No. 5,750,385 and Canadian Patent 132 1563); light repressible promoters (eg. see New Zealand Patent 508103 and U.S. Pat. No. 5,639,952).

"Tissue specific promoters" include promoters which are preferentially or specifically expressed in one or more specific cells, tissues or organs in an organism and/or one or more developmental stages of the organism. It should be understood that a tissue specific promoter also be constitutive or inducible.

Examples of plant tissue specific promoters include: root specific promoters such as those described in US Patent Application 2001047525; fruit specific promoters including ovary specific and receptacle tissue specific promoters such as those described in European Patent 316 441, U.S. Pat. No. 5,753,475 and European Patent Application 973 922; and seed specific promoters such as those described in Australian Patent 612326 and European Patent application 0 781 849 and Australian Patent 746032.

In some embodiments, a promoter which preferentially or specifically directs expression in a root, or one or more parts thereof, may be used. Examples of root-specific or preferential promoters that may be used include the promoter of the root stelar gene AtGRP9 (At2g05440) as described by Chen et al. (*J. Plant Res.* 120: 337-343, 2007) and the root cortex promoter from tobacco as described in U.S. Pat. No. 5,837, 876.

The promoter may also be a promoter that is activatable by one or more transcriptional activators, referred to herein as an "activatable promoter". For example, the activatable promoter may comprise a minimal promoter operably connected to an Upstream Activating Sequence (UAS), which comprises, inter alia, a DNA binding site for one or more transcriptional activators.

As referred to herein the term "minimal promoter" should be understood to include any promoter that incorporates at least an RNA polymerase binding site and, optionally a TATA box and transcription initiation site and/or one or more CAAT boxes. In some embodiments wherein the cell is a plant cell, the minimal promoter may be derived from the Cauliflower Mosaic Virus 35S (CaMV 35S) promoter. The CaMV 35S derived minimal promoter may comprise, for example, a sequence that substantially corresponds to positions −90 to +1 (the transcription initiation site) of the CaMV 35S promoter (also referred to as a −90 CaMV 35S minimal promoter), −60 to +1 of the CaMV 35S promoter (also referred to as a −60 CaMV 35S minimal promoter) or −45 to +1 of the CaMV 35S promoter (also referred to as a −45 CaMV 35S minimal promoter).

As set out above, the activatable promoter may comprise a minimal promoter fused to an Upstream Activating Sequence (UAS). The UAS may be any sequence that can bind a transcriptional activator to activate the minimal promoter. Exemplary transcriptional activators include, for example: yeast derived transcription activators such as Gal4, Pdr1, Gcn4 and Ace1; the viral derived transcription activator, VP16; Hap1 (Hach et al., *J Biol Chem* 278: 248-254, 2000); Gaf1 (Hoe et al., *Gene* 215(2): 319-328, 1998); E2F (Albani et al., *J Biol Chem* 275: 19258-19267, 2000); HAND2 (Dai and Cserjesi, *J Biol Chem* 277: 12604-12612, 2002); NRF-1 and EWG (Herzig et al., *J Cell Sci* 113: 4263-4273, 2000); P/CAF (Itoh et al., *Nucl Acids Res* 28; 4291-4298, 2000); MafA (Kataoka et al., *J Biol Chem* 277: 49903-49910, 2002); human activating transcription factor 4 (Liang and Hai, *J Biol Chem* 272: 24088-24095, 1997); Bcl10 (Liu et al., *Biochem Biophys Res Comm* 320(1): 1-6, 2004); CREB-H (Omori et al., *Nucl Acids Res* 29: 2154-2162, 2001); ARR1 and ARR2 (Sakai et al., *Plant J* 24(6): 703-711, 2000); Fos (Szuts and Bienz, *Proc Natl Acad Sci USA* 97: 5351-5356, 2000); HSF4 (Tanabe et al., *J Biol Chem* 274: 27845-27856, 1999); MAML1 (Wu et al., *Nat Genet* 26: 484-489, 2000).

In some embodiments, the UAS comprises a nucleotide sequence that is able to bind to at least the DNA-binding domain of the GAL4 transcriptional activator.

An example of an activatable promoter includes the enhancer trap system for *Arabidopsis* and rice as described by Johnson et al. (*Plant J.* 41; 779-789, 2005) and Møller et al. (*Plant Cell* 21: 2163-2178, 2009).

In some embodiments, the expression of the CIPK16 nucleic acid is placed under the transcriptional control of a CIPK16 transcriptional control sequence derived from a sodium tolerant plant.

A "CIPK16 transcriptional control sequence" refers to a transcriptional control sequence or promoter which, in its native state, exerts transcriptional control over a CIPK16 nucleic acid.

The term "derived from", as used herein, refers to a source or origin for the transcriptional control sequence or promoter. For example, a transcriptional control sequence "derived from a CIPK16 nucleic acid" refers to a transcriptional control sequence which, in its native state, exerts at least some transcriptional control over a CIPK16 nucleic acid. The term derived from should also be understood to refer to the source of the sequence information for a transcriptional control sequence and not be limited to the source of a nucleic acid itself. Thus, a transcriptional control sequence derived from a CIPK16 nucleic acid need not necessarily be directly isolated from the gene. For example, a synthetic nucleic acid having a sequence that is determined with reference to a transcriptional control sequence which, in its native state, exerts at least some transcriptional control over a CIPK16 nucleic acid should be considered derived from a CIPK16 nucleic acid.

As set out above, the CIPK16 transcriptional control sequence may be derived from a sodium tolerant plant. In some embodiments the term "sodium tolerant plant" may include any plant which exhibits a higher degree of sodium tolerance than the plant into which the transcriptional control sequence is being introduced. In further embodiments, the term sodium tolerant plant refers to particular cultivars or ecotypes within a plant species that exhibit a higher degree of sodium tolerance than at least one other cultivar or ecotype within the plant species.

In some embodiments, the term "sodium tolerant plant" may include a halophyte. As referred to herein, a "halophyte" should be understood to include a plant which can tolerate total dissolved solids in irrigation water of at least 5 g/l, at least 10 g/l, at least 15 g/l, at least 20 g/l, at least 25 g/l, at least 30 g/l, at least 40 g/l, at least 50 g/l or at least 60 g/l.

In some embodiments, the CIPK16 nucleic acid is placed is under the transcriptional control of a transcriptional control sequence comprising the nucleotide sequence set forth in SEQ ID NO: 1 or a functionally active fragment or variant thereof.

SEQ ID NO: 1 is the nucleotide sequence of the CIPK16 promoter from *Arabidopsis thaliana* ecotype Bay-0. As described later, this *Arabidopsis thaliana* ecotype exhibits increased salinity tolerance relative to *Arabidopsis thaliana* ecotype Shandara.

"Functionally active fragments" of SEQ. FD NO: 1 include fragments of a transcriptional control sequence which direct expression of an operably connected nucleotide sequence in a substantially identical pattern to SEQ ID NO: 1 in at least one plant type. In some embodiments, the fragment comprises at least 200 nt, at least 500 nt, at least 1000 nt or at least 1500 nt from the nucleotide sequence set forth in SEQ ID NO: 1.

"Functionally active variants" of the transcriptional control sequence of the invention include orthologs, mutants, synthetic variants, analogs and the like of SEQ ID NO: 1 which direct expression of an operably connected nucleotide sequence in a substantially identical pattern to SEQ ID NO: 1 in at least one plant type. The term "variant" should be considered to specifically include, for example, orthologous transcriptional control sequences from other organisms; mutants of the transcriptional control sequence; variants of the transcriptional control sequence wherein one or more of the nucleotides within the sequence has been substituted, added or deleted; and analogs that contain one or more modified bases or DNA or RNA backbones modified for stability or for other reasons. "Modified" bases include, for example, tritylated bases and unusual bases such as inosine.

In some embodiments, the functionally active fragment or variant comprises at least 50%, at least 55%, at least 60%, at least 65%, at least 70%, at least 75%, at least 80%, at least 82%, at least 85%, at least 87%, at least 90%, at least 92%, at least 95%, at least 96%, at least 97%, at least 98% or at least 99% nucleotide sequence identity to the nucleotide sequence set forth in SEQ ID NO: 1.

When comparing nucleic acid sequences to calculate a percentage identity, the compared nucleotide sequences should be compared over a comparison window of at least 500 nucleotide residues, at least 1000 nucleotide residues, at least 1500 nucleotide residues or over the full length of SEQ ID NO: 1. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms such the BLAST family of programs as, for example, disclosed by Altschul et al. (1997, supra). A detailed discussion of sequence analysis can be found in Unit 19.3 of Ausubel at al. (1998, supra).

In some embodiments, the functionally active fragment or variant comprises a nucleic acid molecule which hybridises to a nucleic acid molecule defining a transcriptional control sequence of the present invention under stringent conditions. In some embodiments, the functionally active fragment or variant comprises a nucleic acid molecule which hybridises to a nucleic acid molecule comprising the nucleotide sequence set forth in SEQ ID NO: 1 under stringent conditions.

As used herein, "stringent" hybridisation conditions will be those in which the salt concentration is less than about 1.5 M Na ion, typically about 0.01 to 1.0 M Na ion concentration (or other salts) at 7.0 to 8.3 and the temperature is at least 30° C. Stringent conditions may also be achieved with the addition of destabilising agents such as formamide. In some embodiments, stringent hybridisation conditions may be low stringency conditions, medium stringency conditions or high stringency conditions. Exemplary low stringency conditions include hybridisation with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridisation in 40 to 45% formamide, 1.0 M NaCl, 1% SDS at 37° C., and a wash in 0.5× to 1×SSC at 55 to 60° C., Exemplary high stringency conditions include hybridisation in 50% formamide, 1 M NaCl, 1% SDS at 37° C., and a wash in 0.1×SSC at 60 to 65° C. Optionally, wash buffers may comprise about 0.1% to about 1% SDS. Duration of hybridisation is generally less than 24 hours, usually 4 to 12 hours.

Specificity of hybridisation is also a function of post-hybridisation washes, with the critical factors being the ionic strength and temperature of the final wash solution. For DNA-DNA hybrids, the $T_m$ can be approximated from the equation of Meinkoth and Wahl (*Anal. Biochem.* 138: 267-284, 1984), i.e. $T_m=81.5°$ C.$+16.6$ (log M)$+0.41$ (% CC)$-0.61$ (% form)$-500/L$; where M is the molarity of monovalent cations, % GC is the percentage of guanosine and cytosine nucleotides in the DNA, % form is the percentage of formamide in the hybridisation solution, and L is the length of the hybrid in base pairs. The $T_m$ is the temperature (under defined ionic strength and pH) at which 50% of a complementary target sequence hybridises to a perfectly matched probe, $T_m$ is reduced by about 1° C. for each 1% of mismatching; thus, $T_m$, hybridisation, and/or wash conditions can be adjusted to hybridise to sequences of different degrees of complementarity. For example, sequences with ≥90% identity can be hybridised by decreasing the $T_m$ by about 10° C. Generally, stringent conditions are selected to be about 5° C. lower than the thermal melting point ($T_m$) for the specific sequence and its complement at a defined ionic strength and pH. However, high stringency conditions can utilise a hybridisation and/or wash at, for example, 1, 2, 3, or 4° C. lower than the thermal melting point ($T_m$); medium stringency conditions can utilise a hybridisation and/or wash at, for example, 6, 7, 8, 9, or 10° C. lower than the thermal melting point ($T_m$); low stringency conditions can utilise a hybridisation and/or wash at, for example, 11, 12, 13, 14, 15, or 20° C. lower than the thermal melting point ($T_m$). Using the equation, hybridisation and wash compositions, and desired $T_m$, those of ordinary skill will understand that variations in the stringency of hybridisation and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridisation of nucleic acids is found in Tijssen (*Laboratory Techniques in Biochemistry and Molecular Biology-Hybridisation with Nucleic Acid Probes*, Pt I, Chapter 2, Elsevier, New York, 1993), Ausubel et al., eds. (*Current Protocols in Molecular Biology*, Chapter 2, Greene Publishing and Wiley-Interscience, New York, 1995) and Sambrook et al., (*Molecular Cloning: A Laboratory Manual* $2^{nd}$ ed., Cold Spring Harbor Laboratory Press, Plainview, N.Y., 1989).

The transcriptional control sequence may also include a terminator. The term "terminator" refers to a DNA sequence at the end of a transcriptional unit which signals termination of transcription. Terminators are 3'-non-translated DNA sequences generally containing a polyadenylation signal, which facilitate the addition of polyadenylate sequences to the 3'-end of a primary transcript. As with promoter sequences, the terminator may be any terminator sequence which is operable in the cells, tissues or organs in which it is intended to be used. Examples of suitable terminator sequences which may be useful in plant cells include: the nopaline synthase (nos) terminator, the CaMV 35S terminator, the octopine synthase (ocs) terminator, potato proteinase inhibitor gene (pin) terminators, such as the pinII and pinIII terminators and the like.

In a second aspect, the present invention provides a method for modulating the salinity tolerance of a multicellular structure comprising a plurality of plant cells, the method comprising modulating the salinity tolerance of one or more plant cells in the multicellular structure according to the method of the first aspect of the invention.

In some embodiments expression of a CIPK16 polypeptide and/or CIPK16 nucleic acid is upregulated in the one or more plant cells and the salinity tolerance of the multicellular structure is increased.

In some embodiments expression of a CIPK16 polypeptide and/or CIPK16 nucleic acid is downregulated in the one or more plant cells and the salinity tolerance of the multicellular structure is decreased.

As referred to herein, a "multicellular structure" includes any aggregation of one or more plant cells as hereinbefore described. As such, a multicellular structure specifically encompasses tissues, organs, whole organisms and parts thereof.

Furthermore, a multicellular structure should also be understood to encompass multicellular aggregations of cultured cells such as colonies, plant calli, liquid or suspension cultures and the like.

In light of the above, the term "multicellular structure" should be understood to include a whole plant, plant tissue, plant organ, plant part, plant reproductive material or cultured plant tissue (eg. callus or suspension culture).

The plants contemplated by the second aspect of the present invention may include any plant including angiosperm or gymnosperm higher plants as well as lower plants such as bryophytes, ferns and horsetails.

In some embodiments, the plant cell may be a monocotyledonous angiosperm plant. In some embodiments, the monocotyledonous plant may be a cereal crop plant as hereinbefore described. In some embodiments, the plant may be a rice plant as hereinbefore described.

In some embodiments, the plant may be a dicotyledonous angiosperm plant as hereinbefore described.

In some embodiments wherein the multicellular structure comprises a plant or a part thereof, modulation of the salinity tolerance of the plant may be effected by modulating the expression of a CIPK16 polypeptide in at least one or more root cells of the plant.

In a third aspect, the present invention provides a genetically modified plant cell having modulated salinity tolerance relative to a wild type form of the plant cell, wherein the expression of a CIPK16 polypeptide and/or a CIPK16 nucleic acid is modulated in the plant cell.

As referred to herein, a "genetically modified cell" comprises a cell that is genetically modified with respect to the wild type of the cell. As such, a genetically modified cell may be a cell which has itself been genetically modified and/or the progeny of such a cell.

The plant cell of the present invention may include a plant cell as hereinbefore described. For example, in some embodiments, the plant cell may be any of an angiosperm, gymnosperm or bryophyte cell. In some embodiments, the cell may be a monocotyledonous angiosperm plant cell, a cereal crop plant cell or a rice cell. In some embodiments the cell may be a dicotyledonous angiosperm plant cell.

As set out above, the expression of a CIPK16 polypeptide and/or a CIPK76 nucleic acid is modulated in the plant cell. Modulation of a CIPK16 polypeptide and/or a CIPK16 nucleic acid may be as described with respect to the first aspect of the invention. In some embodiments, the plant cell of the third aspect of the invention may be produced according to the method of the first aspect of the invention.

In a fourth aspect, the present invention provides a multicellular structure having modulated salinity tolerance, wherein the multicellular structure comprises one or more plant cells according to the third aspect of the invention.

The multicellular structure may be any multicellular structure as hereinbefore described. In some embodiments of the invention the salinity tolerance of the multicellular structure as a whole (eg. a plant) may be modulated relative to a wild type form of the multicellular structure as a result of including one or more cells having modulated salinity tolerance. In some embodiments, the present invention provides a plant having increased salinity tolerance relative to a wild type form of the plant.

In a fifth aspect, the present invention provides a method for ascertaining or predicting the salinity tolerance of a plant cell, the method comprising determining the expression of a CIPK16 polypeptide and/or a CIPK16 nucleic acid in the plant cell.

As described above, the expression of a CIPK16 polypeptide and/or CIPK16 nucleic acid in a plant cell is correlated with the level of salinity tolerance in the plant cell. Thus, relatively high expression of a CIPK16 polypeptide and/or CIPK16 nucleic acid in the plant cell is associated with increased salinity tolerance in the plant cell and low expression of a CIPK16 polypeptide and/or CIPK16 nucleic acid in the plant cell is associated with decreased salinity tolerance in the plant cell.

Methods for determining the level and/or pattern of expression of a nucleic acid or polypeptide are known in the art. Exemplary methods of the detection of RNA expression include methods such as quantitative or semi-quantitative reverse-transcriptase PCR (eg. see Burton et al., *Plant Physiology* 134: 224-236, 2004), in-situ hybridization (eg. see Linnestad et al., *Plant Physiology* 118: 1169-1180, 1998); northern blotting (eg. see Mizuno et al., *Plant Physiology* 132: 1989-1997, 2003); and the like. Exemplary methods for the expression of a polypeptide include Western blotting (eg. see Fido et al., *Methods Mol Biol.* 49: 423-37, 1995); ELISA (eg. see Gendloff et al., *Plant Molecular Biology* 14: 575-583); immunomicroscopy (eg. see Asghar et al., *Protoplasma* 177: 87-94, 1994) and the like. In another embodiment, the expression of a CIPK16 nucleic acid sequence may be determined by determining the number of CIPK16 nucleic acids present in the genomic DNA of one or more cells of the organism.

The plant cells contemplated in the fifth aspect of the invention may include any plant cells as hereinbefore described.

In a sixth aspect, the present invention provides a method for ascertaining or predicting the salinity tolerance of a multicellular structure comprising a plant cell, the method comprising ascertaining or predicting the salinity tolerance of a plant cell in the multicellular structure according to the method of any one of the fifth aspect of the invention.

In some embodiments, the expression of a CIPK16 polypeptide and/or CIPK16 nucleic acid in a plant cell of the multicellular structure is correlated with the level of salinity tolerance in a multicellular structure comprising the plant cell. Thus, relatively high expression of a CIPK16 polypeptide and/or CIPK16 nucleic acid in the plant cell is associated with increased salinity tolerance in the multicellular structure and relatively low expression of a CIPK16 polypeptide and/or CIPK16 nucleic acid in the plant cell is associated with decreased salinity tolerance in the multicellular structure.

The multicellular structures contemplated in the sixth aspect of the invention may include any multicellular structures, including plants or parts thereof, as hereinbefore described.

The cells used for determining the expression of a CIPK16 polypeptide and/or a CIPK16 nucleic acid may be any suitable plant cell. In some embodiments, the cells may comprise a root cell. In some embodiments, the cells may comprise a leaf cell.

In further embodiments, the method of the sixth aspect of the invention may be used to ascertain the salinity sensitivity or tolerance of an organism and then select individual organisms on the basis of the ascertained level of salinity sensitivity or tolerance. For example, in the case of plants, plants having increased salinity tolerance may be selected for planting in saline soils or may be selected for breeding programs to produce salinity tolerant cultivars of the plant.

Finally, reference is made to standard textbooks of molecular biology that contain methods for carrying out basic techniques encompassed by the present invention, including DNA restriction and ligation for the generation of the various genetic constructs described herein. See, for example, Maniatis et al., *Molecular Cloning: A Laboratory Manual* (Cold Spring Harbor Laboratory Press, New York, 1982) and Sambrook et al. (2000, supra).

Embodiments of the present invention are further described by the following non-limiting examples:

EXAMPLE 1

Figure 1:
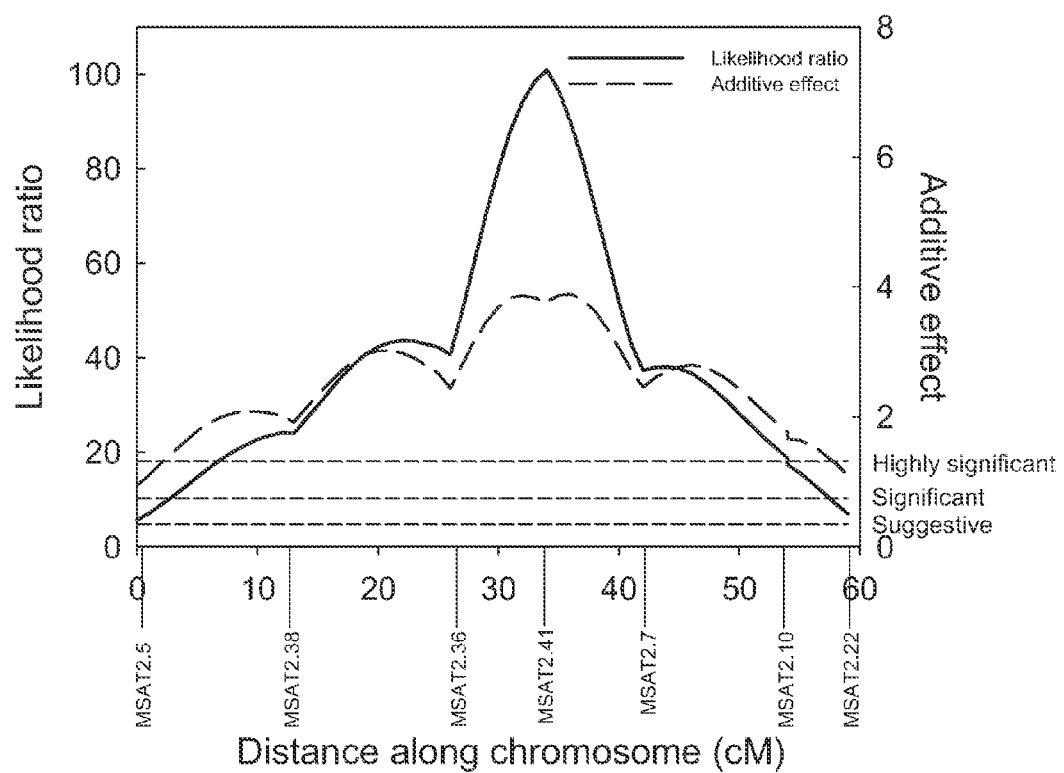
FIG. 1 shows the quantitative trait locus linked to $Na^+$ leaf exclusion on chromosome 2 as plotted on a LR scale. 420 lines of a Bay-0×Shandara mapping population were grown for 6 weeks in soil and supplied with 2 mM at 2, 3, 4, 5 and 6 weeks. Depending on germination and survival between 1 and 8 replicates were made for each line. The black line shows the likelihood ratio statistic and the long dashed line the additive effect. The short dashed lines indicate levels of significance of, from bottom to top, suggestive, significant and extremely significant.

Growth and Phenotyping of Bay-0×Shandara Mapping Population

Phenotyping for $Na^+$ exclusion was performed on 420 recombinant inbred lines (RILs) of a Bay-0×Shandara *Arabidopsis thaliana* mapping population obtained from the European *Arabidopsis* Stock Centre (Nottingham, UK). Plants were germinated on an artificial soil mix composed of 3.6 L Coira, 3.6 L perlite and 0.25 L sand and supplied with 300 ml of nutrient solution (2 mM $Ca(NO_3)$, 15 mM $KNO_3$, 0.5 mM $MgSO_4$, 0.5 mM $NaH_2PO_4$, 15 mM $NH_4NO_3$, 2.5 μM NaFeEDTA, 200 μM $H_3BO_3$, 0.2 μM $Na_2MoO_4$, 0.2 μM $NiCl_2$, 1 μM $ZnSO_4$, 2 μM $MnCl_2$, 2 μM $CuSO_4$ and 0.2 μM $CoCl_2$). After one week, and for the next 5 weeks, the plants were supplied once a week with 300 ml of nutrient solution containing 2 mM NaCl. An additional 300 ml of water was supplied once a week if required with excess water removed after 24 h.

After 6 weeks of growth, the last fully expanded leaf was removed and its fresh weight obtained. The leaf was digested in overnight 1% nitric acid at 85° C. in a hotblock (Thermoline Scientific, Northgate, Australia). Once cooled, samples were diluted as necessary before the Na$^+$ and K$^+$ concentrations in the tissue were determined by flame photometry (Model 420, Sherwood Scientific, Cambridge, UK).

EXAMPLE 2

QTL Mapping

Genotype data for 38 microsatellite markers of all 420 lines was obtained from dbsgap.versailles.inra.fr/vnat/Documentation/33/DOC.html. These data, in addition to the phenotypic data was entered into the mapping programme Map-Manager QTX (mapmanager.org/). Interval mapping, with 1000 permutations, was performed for shoot Na$^+$ and K$^+$ concentrations as well as shoot Na$^+$/K$^+$ ratios.

EXAMPLE 3

DNA Extraction from RILs

DNA was extracted from RILs with recombination occurring between the flanking markers of the QTL. Leaf tissue was frozen in liquid nitrogen and then ground to powder using a mortar and pestle. 400 µl of Edwards buffer (200 mM Tris HCl (pH 7.5), 250 mM NaCl, 25 mM EDTA and 0.5% SDS) was added to the ground plant material and the sample left at room temperature (RT) for 1 hr. The extract was spun at 10,000 g for 1 min and 300 µl of supernatant added to 300 µl of iso-propanol. Samples were left for 2 mM at RT and then spun at 10,000 g for 5 mins. The supernatant was removed and the pellet resuspended overnight at 4° C. in 200 µl TE buffer. The samples were centrifuged at 10,000 g for 5 mins before 150 µl of suspension was added to 15 µl of 3 M NaAc and 115 µl of iso-propanol. Samples were left at room temperature for 10 min before being spun at 10,000 g for 5 min. The supernatant was removed and the DNA pellet washed twice with 70% ethanol before left to air dry. The DNA was resuspended in 100 µl TE buffer.

EXAMPLE 4

Fine Mapping of QTL

To fine map the QTL, 20 cleaved amplified polymorphic site (CAPS) markers were designed to recognise the difference between Bay-0 and Shandara DNA in the QTL interval. Each CAPS marker was designed to amplify a region of genomic DNA between 500-1000 bases long which had within it a restriction site for a specific restriction enzyme on one parent's DNA but not the other. Polymerase chain reaction (PCR) using specific CAPS marker primers and Platinum Taq (Invitrogen, Carlsbad, Calif., USA) was carried out on all DNA and the PCR product digested for 3 hrs with the required restriction enzyme. Genotypes of the mapping lines for the new CAPS markers were visualised on a 2% agarose gel.

EXAMPLE 5

Mining Online Microarray Data

Genevestigator version 3 (genevestigator.ethz.ch/gv/index.jsp) was used to mine 3110 *Arabidopsis* Affymetrix ATH1: 22 k microarrays for the expression profile of AtCIPK16 (At2g25090) in different plant tissues and under different experimental conditions.

EXAMPLE 6

Q-PCR Hydroponics

Seeds of *Arabidopsis thaliana* ecotypes Columbia (Col), Wassilewskija (Ws) and Landsberg erecta (Ler) were obtained from the European *Arabidopsis* Stock Centre (Nottingham, UK). Individual seeds were germinated in 1.5 ml microfuge tubes on top of 0.8% bactoagar supplemented with half strength *Arabidopsis* nutrient media (Arteca and Arteca, *Physiologia Plantarum* 108: 188-193, 2000). After 2 d vernalisation at 4° C. the tubes were transferred to a growth room with a 10 h light/14 h dark photoperiod, an irradiance of 70 µmol·m$^{-2}$·s$^{-1}$, and a constant temperature of 21° C. When the plant's roots had grown two-thirds of the distance through the agar the bottom of the microfuge tubes were removed allowing the roots to emerge. Upon emergence of the root from the tube they were transferred to a continually aerated hydroponics setup containing full strength nutrient solution. The pH of the hydroponic solution was monitored and maintained at pH 5.7. Salt stress was applied 5 weeks after germination by the addition of 50 or 100 mM NaCl and calcium activity, as calculated using Visual Minteq V 2.3 (US Environmental Protection Agency; USA), was maintained in the nutrient solution by additional CaCl$_2$ if required. Whole roots and shoots were harvested after 5 d of salt treatment and immediately frozen in liquid nitrogen.

EXAMPLE 7

Expression Analysis of CIPK16 in Hydroponically Grown Plants

Total RNA was extracted from frozen root and shoot samples using TRIzol reagent (Invitrogen, Carlsbad, Calif., USA), following the protocol described previously (Chomczynski, *BioTechniques* 15: 532-537, 1993). Genomic DNA contamination was removed using Ambion's DNA-free (Promega, Madison, Wis., USA) and 200 ng of total RNA was used to synthesis cDNA using Superscript III (Invitrogen, Carlsbad, Calif., USA). Quantitative real-time PCR (Q-PCR) was performed on the cDNA for the gene AtCIPK16 (At2g25090) using a RG6000 Rotor-Gene Real Time Thermal Cycler (Corbett Research, Sydney, Australia) according to the method of Burton et al. (*Plant Physiol.* 134: 224-236, 2004). Cyclophilin (At2g36130), Tubulin alpha 2 chain (TUA2, At1g50010) and glyceraldehyde 3-phosphate dehydrogenase A (GAPA, At3g26650) were used as control genes to normalise the results. The results presented are the average±s.e.m. for three biological replicates. For primer sequences see table 2 below.

TABLE 2

Primers used for Q-PCR experiments

| Gene name | Forward or reverse primer | Primer sequence (5' → 3') | SEQ ID NO: |
|---|---|---|---|
| AtCIPK16 | Forward | TGATGTGATGAATTGGAAGGCG | 2 |
|  | Reverse | ACTCTCAAGATTGCTTGTGCCG | 3 |
| AtCyclophilin | Forward | TGGCGAACGCTGGTCCTAATACA | 4 |
|  | Reverse | CAAAAACTCCTCTGCCCCAATCAA | 5 |
| AtTUA2 | Forward | ATGTGGGTCAGGGTATGGAA | 6 |
|  | Reverse | CCGACAACCTTCTTAGTCTCCTCT | 7 |

TABLE 2-continued

Primers used for Q-PCR experiments

| Gene name | Forward or reverse primer | Primer sequence (5' → 3') | SEQ ID NO: |
|---|---|---|---|
| AtGAPA | Forward | TGGTTGATCTCGTTGTGCAGGTCTC | 8 |
| | Reverse | GTCAGCCAAGTCAACAACTCTCTG | 9 |

EXAMPLE 8

Novel QTL Detected on Chromosome 2

Figure 2:
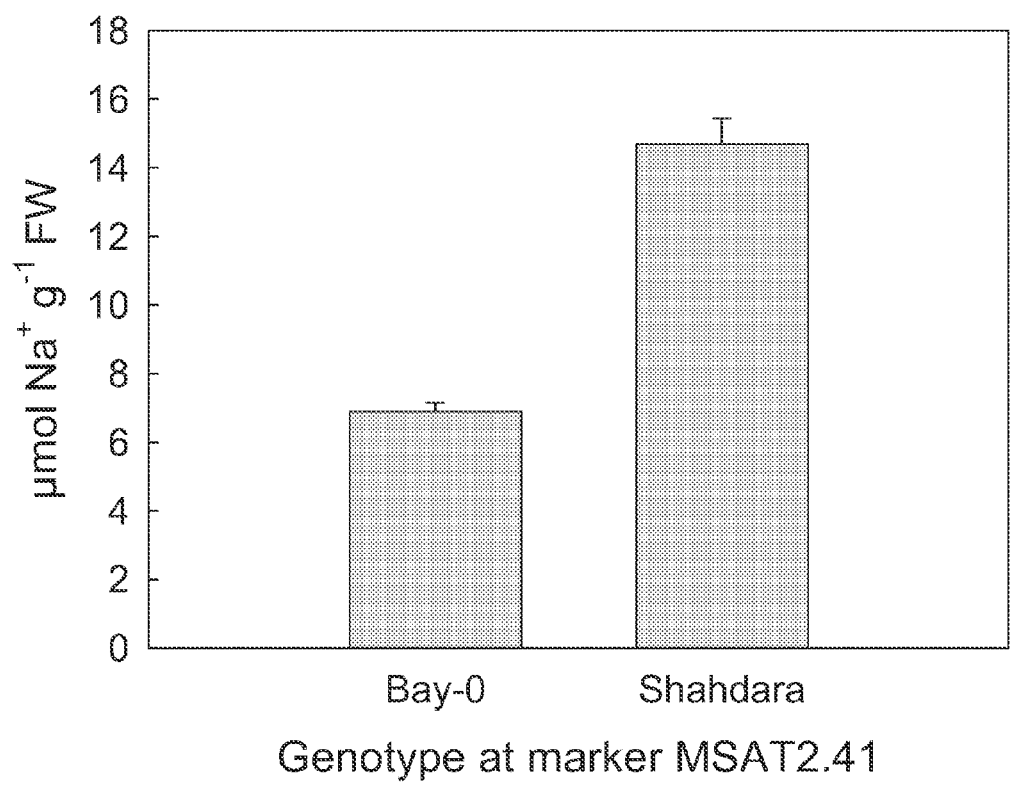
FIG. 2 shows $Na^+$ concentrations, as determined by flame photometry, in lines of the Bay-0×Shandara mapping population with either the Bay-0 or Shandara genotype at the marker MSAT2.41 which lies under the QTL peak. Results are the mean±s.e.m. (n=228 for Bay-0 genotypes and n=133 for Shandara genotypes).

Shoot Na$^+$ and K$^+$ accumulation was collected from 6 week old *Arabidopsis* RILs that had been watered with 2 mM NaCl at 2, 3, 4, 5 and 6 weeks. For each line that germinated the number of replicates was between 1 and 8 depending on plant survival. The phenotypic data along with the RIL genotypic data downloaded from the web was entered into MapManager and used for QTL mapping. Using interval mapping, an extremely significant QTL explaining 24% of the total phenotypic variation with a likelihood ratio (LR) of 100.9 was found at the microsatellite marker MSAT2.41 between the flanking markers MSAT2.36 and MSAT2.7 on chromosome 2 (see FIG. 1 and Table 3 below). When the RILs are separated by genotype between those with a Bay-0 or Shandara allele at MSAT2.41 it can be found that there is approximately a two-fold difference in Na$^+$ accumulation between the lines. Those RILs with a Bay-0 allele at MSAT2.41 have a mean Na$^+$ shoot concentration of 6.9±0.25 μmoles Na$^+$ g$^{-1}$ FW, n=228, while those with a Shandara allele have 14.7±0.74 μmoles Na$^+$ g$^{-1}$FW, n=133, results are the mean±standard error of the mean (s.e.m.) (FIG. 2).

TABLE 3

Interval mapping results calculated from Na$^+$ exclusion phenotype and RIL genotype data.

| Marker Name | Position on Chromosome (cM) | Likelihood ratio | % total phenotypic variation | Additive effect |
|---|---|---|---|---|
| MSAT2.5 | 0 | 5.7 | 2 | 0.95 |
| | 1 | 7.2 | 2 | 1.11 |
| | 2 | 8.9 | 2 | 1.29 |
| | 3 | 10.7 | 3 | 1.46 |
| | 4 | 12.7 | 3 | 1.63 |
| | 5 | 14.8 | 4 | 1.78 |
| | 6 | 16.8 | 5 | 1.91 |
| | 7 | 18.6 | 5 | 2 |
| | 8 | 20.2 | 5 | 2.06 |
| | 9 | 21.6 | 6 | 2.09 |
| | 10 | 22.7 | 6 | 2.09 |
| | 11 | 23.6 | 6 | 2.06 |
| | 12 | 24.2 | 6 | 2.01 |
| MSAT2.38 | 13 | 24 | 6 | 1.92 |
| | 14 | 27 | 7 | 2.13 |
| | 15 | 30 | 8 | 2.34 |
| | 16 | 33.1 | 9 | 2.54 |
| | 17 | 36.1 | 9 | 2.72 |
| | 18 | 38.7 | 10 | 2.87 |
| | 19 | 40.8 | 11 | 2.97 |
| | 20 | 42.4 | 11 | 3.02 |
| | 21 | 43.3 | 11 | 3.02 |
| | 22 | 43.7 | 11 | 2.98 |
| | 23 | 43.5 | 11 | 2.9 |
| | 24 | 43 | 11 | 2.79 |
| | 25 | 42.2 | 11 | 2.67 |
| MSAT2.36 | 26 | 40.7 | 10 | 2.44 |
| | 27 | 50.2 | 13 | 2.81 |
| | 28 | 60.4 | 15 | 3.17 |
| | 29 | 70.6 | 17 | 3.47 |
| | 30 | 80.1 | 19 | 3.69 |
| | 31 | 88.1 | 21 | 3.83 |
| | 32 | 94.2 | 22 | 3.87 |
| | 33 | 98.4 | 23 | 3.83 |
| MSAT2.41 | 34 | 100.9 | 24 | 3.77 |
| | 35 | 96.5 | 23 | 3.87 |
| | 36 | 89.9 | 21 | 3.89 |
| | 37 | 81.5 | 19 | 3.8 |
| | 38 | 71.9 | 17 | 3.63 |
| | 39 | 61.8 | 15 | 3.37 |
| | 40 | 51.9 | 13 | 3.06 |
| | 41 | 43 | 11 | 2.73 |
| MSAT2.7 | 42 | 37.4 | 10 | 2.46 |
| | 43 | 38 | 10 | 2.6 |
| | 44 | 38.1 | 10 | 2.7 |
| | 45 | 37.7 | 10 | 2.77 |
| | 46 | 36.7 | 9 | 2.8 |
| | 47 | 35.1 | 9 | 2.77 |
| | 48 | 33.1 | 8 | 2.69 |
| | 49 | 30.8 | 8 | 2.58 |
| | 50 | 28.2 | 7 | 2.43 |
| | 51 | 25.7 | 7 | 2.26 |
| | 52 | 23.2 | 6 | 2.09 |
| | 53 | 20.9 | 5 | 1.92 |
| | 54 | 18.8 | 5 | 1.75 |
| MSAT2.10 | 54 | 17.4 | 5 | 1.66 |
| | 55 | 15.7 | 4 | 1.64 |
| | 56 | 13.6 | 4 | 1.56 |
| | 57 | 11.4 | 3 | 1.44 |
| | 58 | 9.1 | 2 | 1.28 |
| MSAT2.22 | 59 | 7.1 | 2 | 1.1 |

Columns show microsatellite marker position, likelihood score of DNA region's effect on Na$^+$ exclusion phenotype, % total phenotypic variation explained by region and the additive effect.

EXAMPLE 9

Fine Mapping of QTL

Between the flanking markers MSAT2.36 and MSAT2.7 there were approximately 1200 genes with no obvious candidate gene involved in Na$^+$ transport, such as AtSOS1, AtNHX1, AtHKT1;1 or AtAVP1. In order to narrow the interval to a smaller number of genes, 20 CAPS markers were designed and used to genotype the RILs with recombination between the two flanking markers. Fine mapping narrowed the interval of the QTL to between the genes At2g24970 and At2g25355, a region containing 41 genes (see Table 4, below). Within this region is a candidate gene of interest AtCIPK16 (At2g25090) which encodes a Calcineurin B-like interacting protein kinase and belongs to the same family of genes as AtCIPK24 (At5g35410), also known as AtSOS2.

TABLE 4

The number of candidate genes remaining in the QTL interval, along with a brief description of each gene.

| Gene locus | Description |
|---|---|
| AT2G24970.1 | expressed protein | |
| AT2G24980.1 | proline-rich extensin-like family |
| AT2G24990.1 | RIO1 family protein, similar to |

TABLE 4-continued

The number of candidate genes remaining in the QTL interval, along with a brief description of each gene.

| Gene locus | Description |
| --- | --- |
| AT2G25000.1 | WRKY family transcription factor, |
| AT2G25010.1 | expressed protein | |
| AT2G25050.1 | formin homology 2 |
| AT2G25060.1 | plastocyanin-like |
| AT2G25070.1 | protein phosphatase 2C, putative/ |
| AT2G25080.1 | phospholipid hydroperoxide |
| AT2G25090.1 | CBL-interacting protein kinase 16 |
| AT2G25100.1 | ribonuclease HII family protein, |
| AT2G25110.1 | MIR domain-containing protein, |
| AT2G25120.1 | bromo-adjacent homology (BAH) |
| AT2G25130.1 | armadillo/beta-catenin repeat |
| AT2G25140.1 | heat shock protein 100, putative/ |
| AT2G25150.1 | transferase family protein, |
| AT2G25160.1 | cytochrome P450, putative, similar |
| AT2G25170.1 | chromatin remodeling factor CHD3 |
| AT2G25180.1 | two-component responsive regulator |
| AT2G25185.1 | Encodes a defensin-like (DEFL) |
| AT2G25190.1 | expressed protein | |
| AT2G25200.1 | expressed protein | |
| AT2G25210.1 | ribosomal protein L39 (RPL39A) |
| AT2G25220.1 | protein kinase family protein, |
| AT2G25230.1 | myb family transcription factor |
| AT2G25240.1 | serpin, putative/serine protease |
| AT2G25250.1 | expressed protein | |
| AT2G25260.1 | expressed protein | |
| AT2G25270.1 | expressed protein | |
| AT2G25280.1 | expressed protein | |
| AT2G25290.1 | octicosapeptide/Phox/Bem1p (PB1) |
| AT2G25295.1 | Encodes a member of a family of |
| AT2G25300.1 | similar to galactosyltransferase |
| AT2G25305.1 | Encodes a defensin-like (DEFL) |
| AT2G25310.1 | expressed protein | |
| AT2G25320.1 | meprin and TRAF homology |
| AT2G25330.1 | meprin and TRAF homology |
| AT2G25340.1 | synaptobrevin family protein, |
| AT2G25344.1 | Encodes a member of a family of |
| AT2G25350.1 | phox (PX) domain-containing |
| AT2G25355.1 | exonuclease-related, |

AtCIPK16 is shown in bold.

EXAMPLE 10

Specificity and Inducibility of CIPK16 Expression

Figure 3:
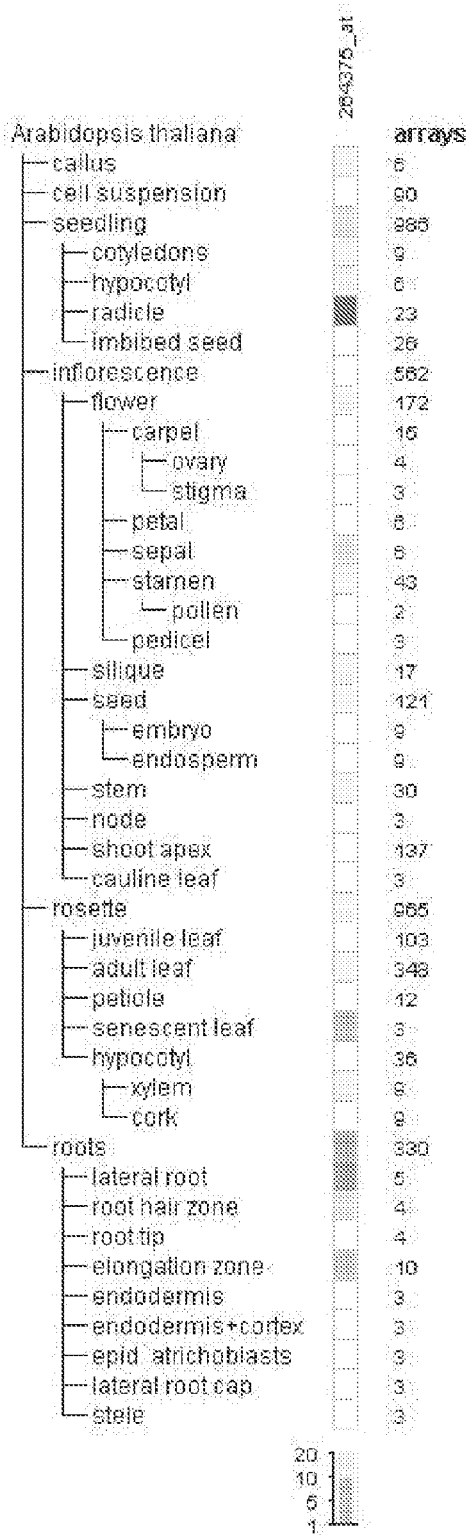
FIG. 3 shows a Genevestigator heatmap output for the expression profile of AtCIPK16 in different tissues of *Arabidopsis*. White and light gray indicate no or low gene expression, darker gray indicates high expression. The number of arrays mined for each tissue are listed.
Figure 4:
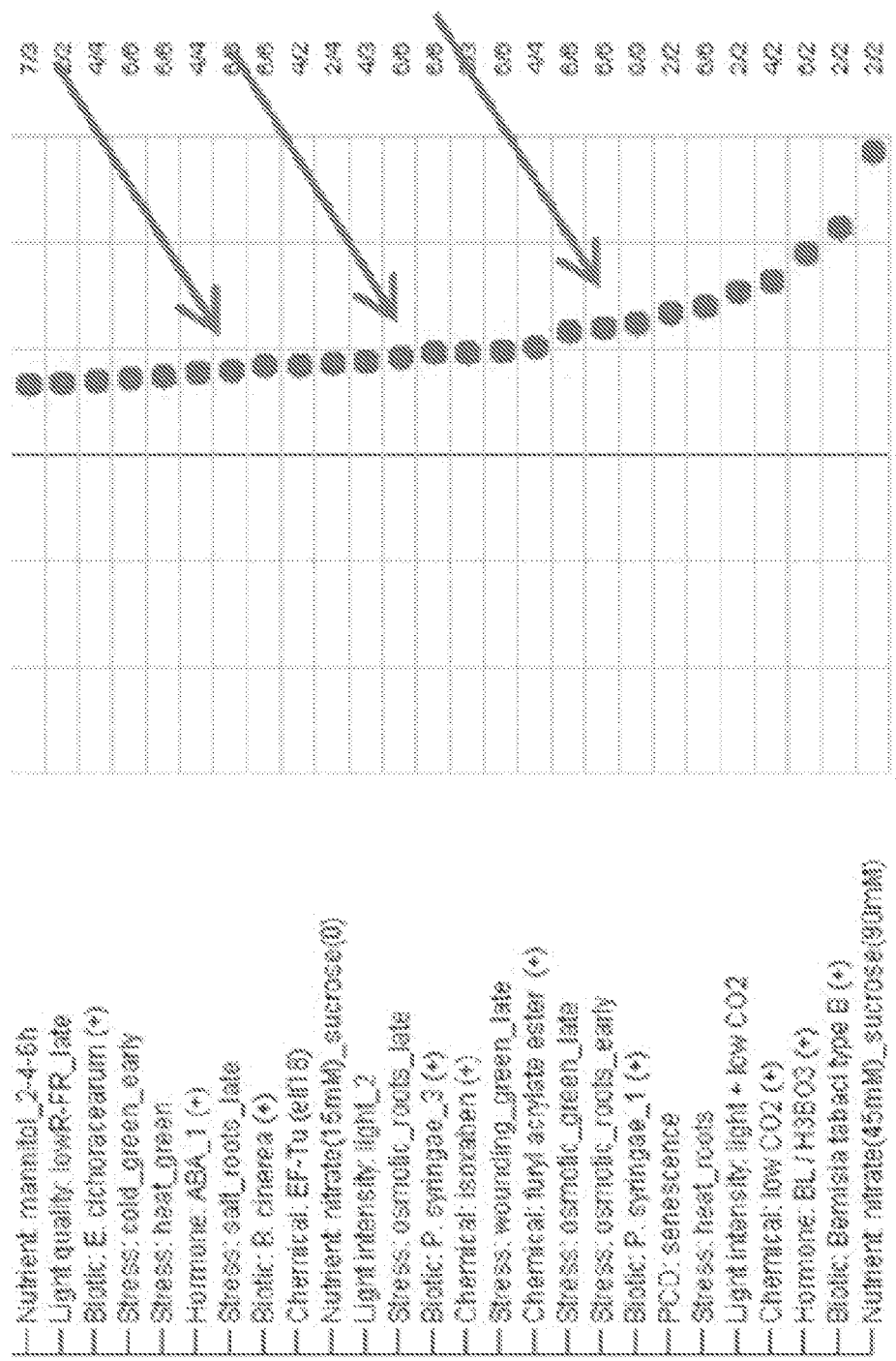
FIG. 4 shows a partial Genevestigator dot plot output for the increase in the expression of AtCIPK16 in different experimental conditions. Arrows indicate salt and osmotic stress experiments. The number of arrays mined for each tissue are listed (experimental/control).

Searches using Genevestigator revealed that AtCIPK16 is primarily expressed in root tissue and younger plants, such as seedlings (see FIG. 3). Very little gene expression is found in the shoot. A number of environmental stimuli were found to increase the expression of AtCIPK16 in the root, including salinity and osmotic stress (see FIG. 4).

EXAMPLE 11

Expression of AtCIPK16 in Hydroponically Grown *Arabidopsis* Ecotypes

Figure 5:
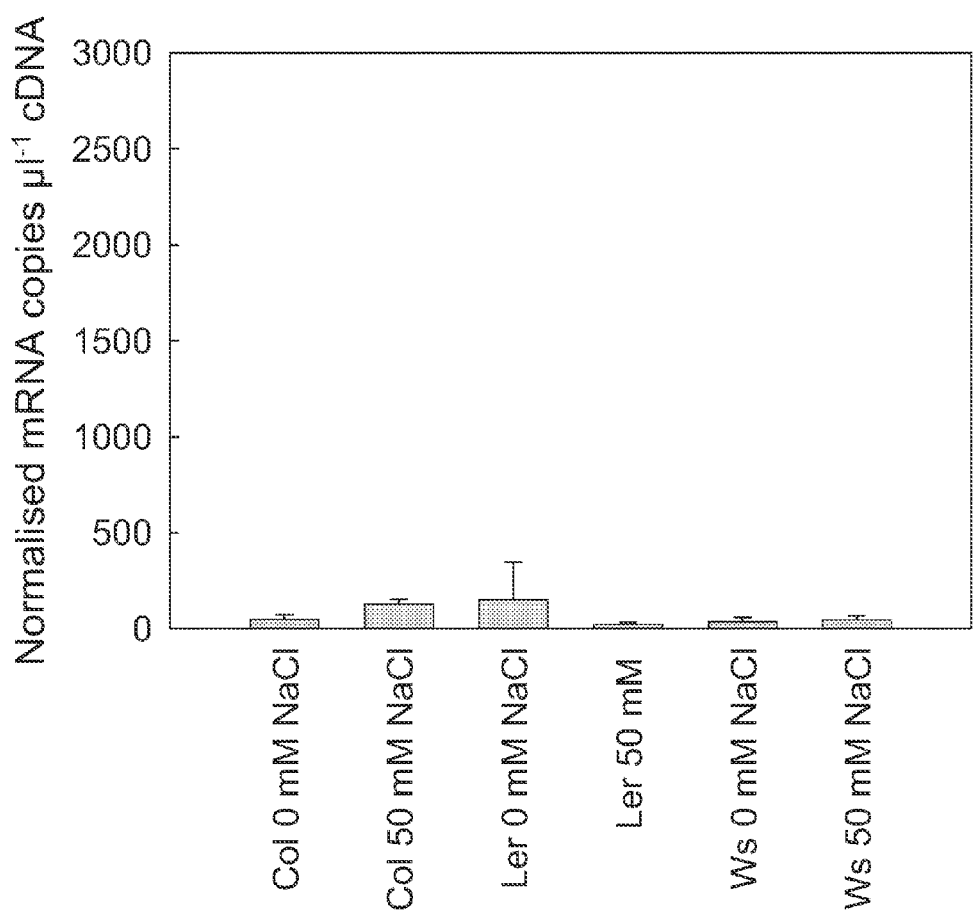
FIG. 5 shows the level of gene expression of AtCIPK16 in the shoots of three *Arabidopsis* ecotypes grown for 5 weeks in hydroponics and then exposed to 5 days of either 0 or 50 mM NaCl. Results are the mean±s.e.m. (n=3)
Figure 6:
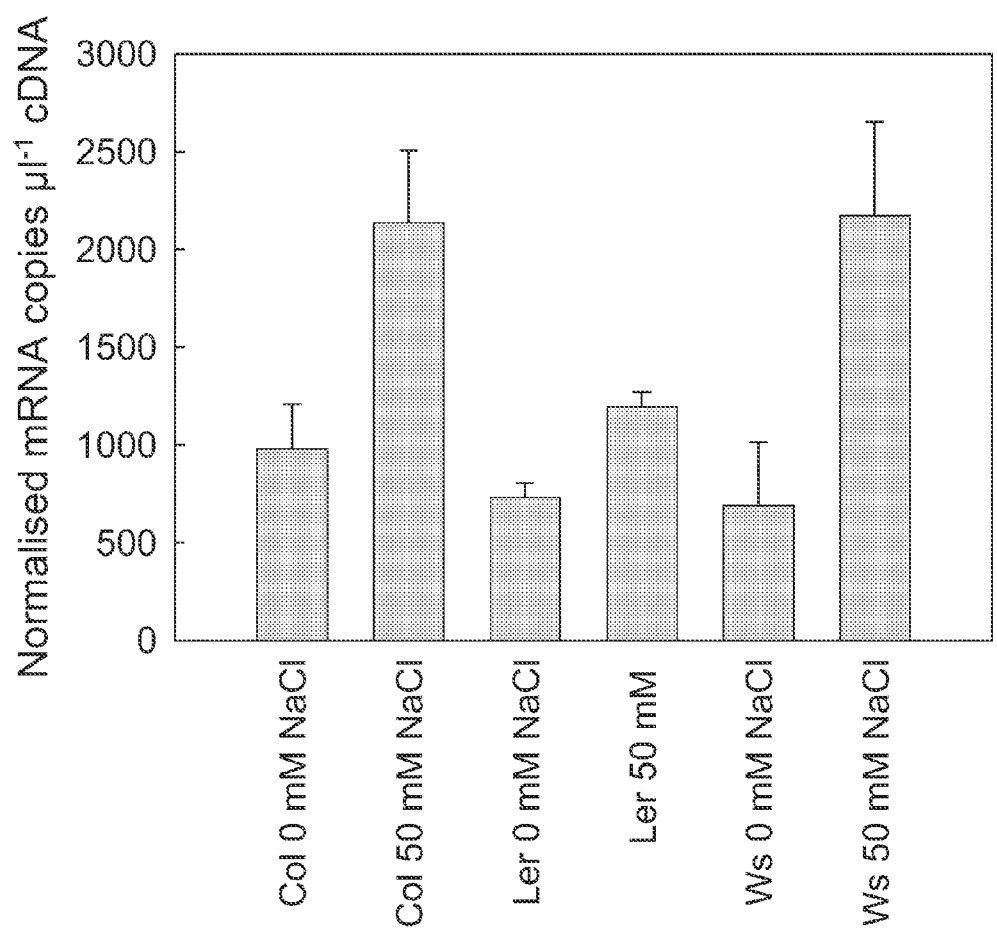
FIG. 6 shows the level of gene expression of AtCIPK16 in the roots of three *Arabidopsis* ecotypes grown for 5 weeks in hydroponics and then exposed to 5 days of either 0 or 50 mM NaCl. Results are the mean±s.e.m. (n=3)
Figure 7:
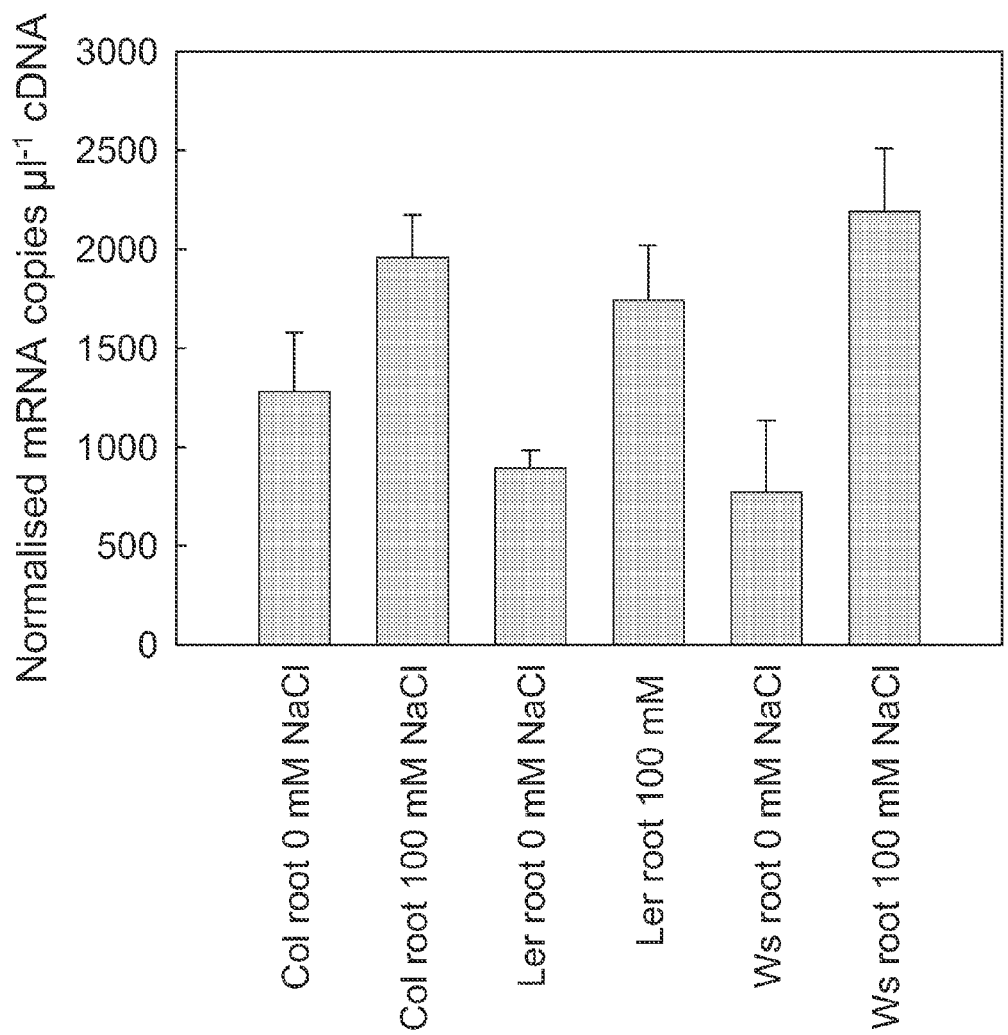
FIG. 7 shows the level of gene expression of AtCIPK16 in the roots of three *Arabidopsis* ecotypes grown for 5 weeks in hydroponics and then exposed to 5 days of either 0 or 100 mM NaCl. Results are the mean±s.e.m. (n=3).

Three cultivars of *Arabidopsis* Col, Ler and Ws were grown hydroponically for five weeks before being exposed to 0, 50 or 100 mM NaCl for 5 days. While no significant expression of AtCIPK16 could be detected in the shoot of any ecotype, under either control or salt stressed conditions (see FIG. 5), there was a significant up-regulation of gene expression in the roots of all ecotypes under both 50 and 100 mM NaCl salt stress (see FIGS. 6 and 7, respectively). Depending on ecotype and NaCl concentration, there was a 1.5 to 3.1-fold increase in AtCIPK16 expression.

EXAMPLE 12

DNA and RNA Extractions and cDNA Synthesis from Wild Type and Transgenic *Arabidopsis* and Rice Plants Genomic DNA was extracted from young leaves of *Arabidopsis thaliana* using the methodology of Edwards et al. (*Nucleic Acids Res* 19: 1349, 1991), Briefly, plant shoot or root tissue was snap frozen in liquid nitrogen and ground to a fine powder using a mortar and pestle. To the powder, 400 µl of Edwards buffer (200 mM Tris pH 8, 25 mM EDTA, 250 mM NaCl and 0.5% SDS), was added and the samples left at room temperature for 1 hr. The samples were centrifuged at 13,000 g for 2 mins and the supernatant removed. DNA was precipitated by the addition of 300 µl of 100% isopropanol, followed by incubation of the samples at room temperature for 2 mins, before centrifugation at 13,000 g for 5 mins. DNA pellets were washed with 70% ethanol and allowed to air dry before being resuspended in 100 µl of TE buffer.

Total RNA was extracted using TRIzol reagent (Invitrogen, Carlsbad, Calif., USA), following the protocol described by Chomczynski (*Biotechniques* 15: 532-537, 1993). Genomic DNA contamination was removed using DNA-free (Ambion, Madison, Wis., USA) and 2 µg of total RNA was used to synthesis cDNA using Superscript III (Invitrogen).

EXAMPLE 13

Over-Expression of AtCIPK16 in *Arabidopsis* and Rice

Using primers AtCIPK16 Whole gene Forward (ATG-GAAGAATCAAACCGTAGTAGTACTGTC; SEQ ID NO: 10) and AtCIPK16 Whole gene Reverse (TTGGAATTG-GATGTGCGAGG; SEQ ID NO: 11), the gene of AtCIPK16 (2069 nucleotides) was cloned from *Arabidopsis* genomic DNA into a pCR8 Gateway enabled entry vector. Restriction digestion and sequencing of the plasmid was used to confirm the orientation of the gene in the vector and to ensure there were no errors in the coding sequence of the cloned gene.

For *Arabidopsis* transformation the gene was then transferred into a pTOOL2 destination vector, using a Gateway reaction, and transformed into *Agrobacterium tumefaciens*, strain AGL1.

For rice transformation, the gene was transferred into a pMDC32 destination vector using a Gateway reaction, and transformed into *A. tumefaciens*, strain AGL1. Both of these vectors used a double CaMV35S promoter to drive the expression of the transgene.

EXAMPLE 14 amiRNA Knockdowns

Unlike most *Arabidopsis* genes, there are no commercially available T-DNA insertion knockout mutants available for AtCIPK16. Earlier experimentation in the laboratory investigated whether a GABI-Kat (Max Planck Institute for Plant Breeding Research, Koeln, Germany) T-DNA insertion 140 bp 5' of the start ATG of AtCIPK16 disrupted the gene's expression. It was found, however, that the T-DNA did not affect the expression of the gene, suggesting plants deficient in AtCIPK16 expression were lethal or did not grow well, Gene knockdown mutants, using an artificial micro RNA construct (amiRNA), were therefore created to investigate the effect of reduced AtCIPK16 expression on shoot $Na^+$ accumulation. Using WMD 2—Web MicroRNA Designer (weigelworld.org/cgi-bin/mirnatools.pl), two 21 nucleotide sequences of AtCIPK16 were identified to which two independent amiRNA constructs could be designed which would reduce the expression of the gene. These constructs were designated amiRNA AtCIPK16-1 (TTTTCGTCGATAAACGGCAAG; SEQ ID NO: 12) and amiRNA AtCIPK16-2 (TTATTCCGTAAAACCTCCGGC; SEQ ID NO: 13). Primers (see Table 5) containing the necessary sequences to generate 21 bp amiRNAs were incorporated into the amiRNA vector MIR319a and the whole amiRNA constructs were cloned into pCR8, following the protocol at weigelworld.org/cgi-bin/mirnatools.pl?page=7. After sequencing, to check for any sequence errors and to determine the correct orientation of the sequence, a Gateway LR was performed to transfer the two amiRNA constructs into pTOOL2 vectors which would use a CaMV35S promoter to drive the expression of the amiRNA.

TABLE 5

Primer sequences used to incorporate an amiRNA sequence into vector

| Target | Primer | Primer sequence ('5 → 3') | SEQ ID NO: |
|---|---|---|---|
| amiRNA AtCIPK16-1 | I miR-s | GATTTTCGTCGATAAACGGCAGGTCTCTCTTTTGTATTCC | 14 |
| | IImiR-a | GACCTGCCGTTTATCGACGAAATCAAAGAGAATCAATGA | 15 |
| | III miR*s | GACCCGCCGTTTATCCACGAAATTCACAGGTCGTGATATG | 16 |
| | IV miR*a | GAATATTCCCTAAAACCTCCTGCTCTACATATATATTCCT | 17 |
| amiRNA AtCIPK16-2 | I miR-s | GATTATTCCGTAAAACCTCCCGCTCTCTCTTTTGTATTC | 18 |
| | IImiR-a | GAGCGGGAGGTTTTACGGAATAATCAAAGAGAATCAATGA | 19 |
| | III miR*s | GAGCAGGAGGTTTTAGGGATATTCACAGGTCGTGATATG | 20 |
| | IV miR*a | GAATATTCCCTAAAACCTCCTGCTCTACATATATATTCCT | 21 |
| MIR319a | Primer A | CTGCAAGGCGATTAAGTTGGGTAAC | 22 |
| | Primer B | GCGGATAACAATTTCACACAGGAAACA | 23 |

EXAMPLE 15

Arabidopsis Transformations

Arabidopsis Col-0 ecotype was transformed via the floral dip method (Clough and Bent, Plant J 16: 735-743, 1998), using Agrobacterium tumefaciens, strain AGL1, with the pTOOL2 vectors containing either the 35S over-expression or amiRNA construct. Seeds were collected from transformed plants and germinated on an artificial soil medium (3.6 L perlite-medium grade, 3.6 L coira and 0.25 L river sand) and sprayed with 100 mg $L^{-1}$ BASTA (AgrEvo, Düsseldorf, Germany) to identify putative $T_1$ transformants. Transformants were transferred to soil, watered weekly with 300 ml of nutrient solution (2 mM Ca(NO$_3$), 15 mM KNO$_3$, 0.5 mM MgSO$_4$, 0.5 mM NaH$_2$PO$_4$, 15 mM NH$_4$NO$_3$, 2.5 µM NaFeEDTA, 200 µM H$_3$BO$_3$, 0.2 µM Na$_2$MoO$_4$, 0.2 µM NiCl$_2$, 1 µM ZnSO$_4$, 2 µM MnCl$_2$, 2 µM CuSO$_4$ and 0.2 µM CoCl$_2$) and grown to flowering to collect $T_2$ seed. DNA and RNA were extracted from $T_1$ plants to determine the presence and expression of the transgene and the number of inserts determined by restriction digests and southern blots.

EXAMPLE 16

Determination of Presence and Activity of Transgene

PCR reactions to determine the presence and activity of the AtCIPK16 transgene or the amiRNA constructs were performed on DNA and cDNA obtained from the transgenic plants. Reactions were performed using Platinum Taq (Invitrogen, Carlsbad, Calif., USA) following the manufacturer's protocol using the primers listed in Table 6, below:

TABLE 6

Primer sequences used to confirm presence of transgene in transformant Arabidopsis and rice plants.

| Target | Primer | Primer sequence ('5 → 3') | SEQ ID NO: |
|---|---|---|---|
| AtCIPK16 | Forward | CATTGATGATGCCAGAAGGGC | 24 |
| | Reverse | AATTCTTTGTTCAGGATCCGGC | 25 |
| Hygromycin | Forward | GATGTTGGCGACCTCGTATT | 26 |
| | Reverse | GTGCTTGACATTGGGGAGTT | 27 |
| Basta | Forward | GAAGTCCAGCTGCCAGAAAC | 28 |
| | Reverse | AAGCACGGTCAACTTCCGTA | 29 |
| AtACT2 | Forward | TTGTGTGTGACAAACTCTCTGG | 30 |
| | Reverse | GGCATCAATTCGATCACTCAG | 31 |
| OsGAP | Forward | GGGCTGCTAGCTTCAACATC | 32 |
| | Reverse | TTGATTGCAGCCTTGATCTG | 33 |
| MIR319a | Primer A | CTGCAAGGCGATTAAGTTGGGTAAC | 22 |
| | Primer B | GCGGATAACAATTTCACACAGGAAACA | 23 |

EXAMPLE 17

Determination of Insert Number Using Southern Blots

Genomic DNA (10 µg) was digested for 5 h at 37° C. with 400 U HindIII. Digested DNA was separated on 1% agarose gels and DNA fragments were transferred to a nylon membrane using the method of Southern (Journal of Molecular Biology 98: 503, 1975). The nylon membrane was neutralised in a solution of 2×SSC. Membranes were blotted dry and dried under vacuum at 80° C. prior to probing. Prehybridisation of the membranes was conducted in a 6×SSC, 1×Denhardt's III solution (2% w/v BSA, 2% w/v Ficoll 400 and 2% PVP), 1% (w/v) SDS and 2.5 mg denatured salmon sperm DNA for a minimum of 4 h at 65° C. Hybridisation mixture (10 ml) containing 3×SSC, 1×Denhardt's III solution, 1% (w/v) SDS and 2.5 mg denatured salmon sperm DNA was used to replace the discarded prehybridisation mixture. DNA probes were radiolabelled with [α-$^{32}$P]-dCTP, using a Megaprime DNA labelling kit according to the manufacturer's directions (Amersham, UK). The probe was hybridised for 16 h at 65° C. The membranes were washed sequentially for 20 min at 65° C. in 2×SSC containing 0.1% (w/v) SDS, with 1×SSC/0.1% (w/v) SDS and with 0.5×SSC/0.1% (w/v) SDS. Membranes were blotted dry, sealed in plastic and RX X-ray film was exposed to the membrane at −80° C. for 24-48 h, using an intensifying screen.

EXAMPLE 18

Arabidopsis Salt Stress Assays

Seeds from Col-0 or segregating $T_2$ plants containing either a construct to over-express or knockdown the activity of AtCIPK16 were surface sterilised, by soaking in 70% ethanol for two minutes followed by 3-4 rinses in sterile milli-Q water, before individual seeds were planted in 1.5 ml microfuge tubes filled with half strength *Arabidopsis* nutrient solution (Arteca and Arteca, *Physiol Plantarum* 108: 188-193, 2000) and 0.8% Bactoagar. The seeds were vernalised for 2 d at 4° C. and then transferred to a growth room with a 10 h light/14 h dark photoperiod, an irradiance of 150 µmol $m^{-2}$ $s^{1}$, and a constant temperature of 21° C. The bottom 0.5-0.7 cm of the microfuge tubes were removed after emergence of the cotyledon and the roots of the seedling had grown approximately two-thirds of the way down the length of the tube. Upon emergence of the root from the agar, the plants were transferred to a constantly aerated hydroponics tank containing full strength *Arabidopsis* nutrient solution. The pH of the hydroponic solution was monitored and maintained at pH 5.7. Salt stress was applied 5 weeks after germination by the addition of 100 mM NaCl in 12 hourly increments of 25 mM. Calcium activity in the growth medium was maintained at 0.3 mM at each salt application by addition of the correct amount of calcium, as calculated using Visual Minteq Version 2.3 (US Environmental Protection Agency, USA).

Plants were harvested after 10 days of salt treatment. Whole shoots of control and salt treated plants were excised and fresh weights recorded. The last fully expanded leaf was removed, weighed and digested in 1% nitric acid overnight at 85° C. in a Hot Block (Environmental Express, Mt Pleasant, S.C., USA). $Na^+$ and $K^+$ concentrations in this leaf were measured using a model 420 flame photometer (Sherwood Scientific, Cambridge, UK). For the transgenic plants containing either the 35S over-expression or amiRNA constructs, the remainder of the shoot and root material was frozen in liquid nitrogen for DNA and RNA extractions to confirm presence and activity of the transgene.

EXAMPLE 19

Semi-Quantitative PCR

Semi-quantitative PCR for AtCIPK16 was performed on cDNA obtained from both *Arabidopsis* and rice plants growing in hydroponics. Platinum Taq (invitrogen, Carlsbad, Calif., USA) was used following the manufacturer's protocol and using the primers listed in Table 6.

Briefly, approximately 2 µg of cDNA was added to 1×PlatTaq PCR buffer, 1.5 mM $MgCl_2$, 0.2 mM dNTPs, 0.2 µM Forward primer, 0.2 µM reverse primer and 1 U of PlatinumTaq. Amplification conditions were initial denaturing for 2 mins at 94° C., followed by 28 cycles of 30 sec 94° C., 30 sec 50° C. and 1 min 72° C. The control genes AtACT2 and OsGAP were used for *Arabidopsis* and rice respectively. Samples were run on agarose gels containing SyberSafe for visualisation of DNA and a photograph taken of the gel images. The imaging programme, Scion Image (Scion Corporation, Maryland, USA), was used to determine the intensity of all PCR product bands observed from the gel, as well as the background signal from the gel itself. The background intensity between each gel was first removed and the signal intensity for each control gene from every sample was standardised. The expression of AtCIPK16 for each sample was adjusted accordingly, using the factor necessary to standardise that sample's control gene expression, allowing the comparison between different samples.

EXAMPLE 20

Rice Transformation

Rice seeds were transformed using a modified methodology of Toki at al. (*Plant J.* 47: 969-976, 2006). Wild type Nipponbare rice seeds were dehusked and washed for 1 min with 70% ethanol. The seeds were sterilised for 30 mins in 30% White King bleach, then rinsed ten times with sterile milliQ water. The seeds were transferred onto plates containing N6D media (Toki at al., 2006, supra) and grown in the dark at 28° C. for 5-8 day to induce germination. *A. tumefaciens* transformed with the pMDC32 plasmid containing the AtCIPK16 gene was suspended in AAM media (Toki at al., 2006, supra) and adjusted to an optical density at 600 nm of 0.1. The germinated rice seedlings were dipped into the *A. tumefaciens* containing AAM media for 2 min before being incubated on 2N6-AS media (Toki at al., 2006, supra) in the dark at 25° C. for 3 days. After three days the seeds were rinsed once with sterile water for 1 min and then twice with sterile water containing the antibiotics 400 mg $L^{-1}$ Cefotaxime and 100 mg $L^{-1}$ Vancomycine. Washed seeds were transferred onto N6D-selective media (Table 7), containing 400 mg $L^{-1}$ Cefotaxime, 100 mg $L^{-1}$ Vancomycine and 150 mg $L^{-1}$ Genetacine, and grown in the dark at 28° C. for 3 weeks. Transformed calli were grown for 1 week on PRN media (Table 7) at 28° C. in the dark, 3 days on RN media (Table 7) at 28° C. in the dark and on RN media at 28° C. in the light, until the first shoot appeared. The newly formed shoot was separated from the remaining callus and placed on P media (Table 7) in the light at 28° C. until big enough to transfer to soil. The primary transformants were then grown to seed in a growth room with the following conditions: 28° C./25° C. day/night, 80%/60% day/night humidity and 600 µmol $m^{-2}s^{-1}$ light, with a light dark cycle of 12 hrs light/12 hrs night.

TABLE 7

Rice culture media

| Media | Media constiuent | Amount/1 L |
|---|---|---|
| N6D-selection | $KNO_3$ | 2.83 g |
| | $(NH_4)_2 SO_4$ | 463 mg |
| | $KH_2 PO_4$ | 400 mg |
| | $CaCl_2 2H_2O$ | 165 mg |
| | $MgSO_4 7H_2O$ | 185 mg |
| | $MnSO_4 H_2O$ | 10 mg |
| | $H_3BO_3$ | 3 mg |
| | $ZnSO_4 7H_2O$ | 2 mg |
| | KI | 0.75 mg |
| | $Na_2MoO_4 2H_2O$ | 0.25 mg |
| | $CuSO_4 5H_2O$ | 0.025 mg |
| | $CoCl_2 6H_2O$ | 0.025 mg |
| | $FeSO_4 7H_2O$ | 27.8 mg |
| | $Na_2EDTA$ | 37.3 mg |
| | Nicotonic acid | 0.5 mg |
| | Pyridoxine HCl | 0.5 mg |
| | Thiamine | 5 mg |
| | Casein hydrolisate | 300 mg |
| | Glycine | 2 mg |
| | L-Proline | 2.878 g |
| | myo-Inositol | 100 mg |
| | 2,4-D | 2 mg |
| | Sucrose | 30 g |
| | pH | 5.8 |
| | Gelrite | 4 g |

TABLE 7-continued

Rice culture media

| Media | Media constiuent | Amount/1 L |
|---|---|---|
| | Cefotaxime | 400 mg |
| | Vancomycine | 100 mg |
| | Genetacine | 150 mg |
| P media | Murashige and Skoog media Basal salt mix | 4.3 g |
| | Murashige and Skoog vitamin mix | 103 mg |
| | Sucrose | 50 g |
| | pH | 5.8 |
| | Phytagel | 2.6 g |
| RN media | $KNO_3$ | 2.83 g |
| | $(NH_4)_2 SO_4$ | 463 mg |
| | $KH_2 PO_4$ | 400 mg |
| | $CaCl_2\ 2H_2O$ | 165 mg |
| | $MgSO_4\ 7H_2O$ | 185 mg |
| | $MnSO_4\ H_2O$ | 10 mg |
| | $H_3BO_3$ | 3 mg |
| | $ZnSO_4\ 7H_2O$ | 2 mg |
| | KI | 0.75 mg |
| | $Na_2MoO_4\ 2H_2O$ | 0.25 mg |
| | $CuSO_4\ 5H_2O$ | 0.025 mg |
| | $CoCl_2\ 6H_2O$ | 0.025 mg |
| | $FeSO_4\ 7H_2O$ | 27.8 mg |
| | $Na_2EDTA$ | 37.3 mg |
| | Nicotonic acid | 0.5 mg |
| | Pyridoxine HCl | 0.5 mg |
| | Thiamine HCl | 5 mg |
| | Casein hydrolisate | 300 mg |
| | Glutamine | 500 mg |
| | L-Proline | 500 mg |
| | myo-Inositol | 100 mg |
| | BAP | 3 mg |
| | NAA | 0.5 mg |
| | Sucrose | 30 g |
| | pH | 5.8 |
| | Phytagel | 3.5 g |
| PRN media | $KNO_3$ | 2.83 g |
| | $(NH_4)_2 SO_4$ | 463 mg |
| | $KH_2 PO_4$ | 400 mg |
| | $CaCl_2\ 2H_2O$ | 165 mg |
| | $MgSO_4\ 7H_2O$ | 185 mg |
| | $MnSO_4\ H_2O$ | 10 mg |
| | $H_3BO_3$ | 3 mg |
| | $ZnSO_4\ 7H_2O$ | 2 mg |
| | KI | 0.75 mg |
| | $Na_2MoO_4\ 2H_2O$ | 0.25 mg |
| | $CuSO_4\ 5H_2O$ | 0.025 mg |
| | $CoCl_2\ 6H_2O$ | 0.025 mg |
| | $FeSO_4\ 7H_2O$ | 27.8 mg |
| | $Na_2EDTA$ | 37.3 mg |
| | Nicotonic acid | 0.5 mg |
| | Pyridoxine HCl | 0.5 mg |
| | Thiamine HCl | 5 mg |
| | Casein hydrolisate | 300 mg |
| | Glutamine | 500 mg |
| | L-Proline | 500 mg |
| | myo-Inositol | 100 mg |
| | BAP | 3 mg |
| | NAA | 0.5 mg |
| | ANA | 1 mg |
| | Cefotaxime | 400 mg |
| | Vancomycine | 100 mg |
| | Genetacine | 150 mg |
| | Sucrose | 30 g |
| | pH | 5.8 |
| | Phytagel | 3.5 g |

EXAMPLE 21

Rice Salt Stress Assays

35S::AtCIPK16 and wild type Nipponbare rice seeds were germinated for 5 days on moist filter paper at 28° C./25° C. day/night, 80%/60% day/night humidity and 600 µmol $m^{-2}s^{-1}$ light, with a light dark cycle of 12 hrs light/12 hrs night. Seedlings were removed from the filter paper and placed in 1.5 ml microfuge tribes which had their bottoms removed to allow the roots to emerge from the tube. Each microfuge tube was placed carefully into a support above a 10 l tank filled with ACPFG rice nutrient solution (5 mM $NH_4NO_3$, 5.0 $KNO_3$, 2 mM $Ca(NO_3)_2$, 2.0 mM $MgSO_4$, 0.1 mM $KH_2PO_4$, 0.5 mM $Na_2SiO_3$, 50 µM $NaFe_{(III)}EDTA$, 10 µM $H_3BO_3$, 5 µM $MnCl_2$, 5 µM $ZnSO_4$, 0.5 µM $CuSO_4$ and 0.1 µM $Na_2MoO_3$) allowing the seedlings root access to the media. Seedlings were grown for two weeks in 28° C./25° C. day/night, 80%/60% day/night humidity and 600 µmol $m^{-2}s^{-1}$ light, with a light dark cycle of 12 hrs light/12 hrs night, with the nutrient solution replaced every 5 days. 19 days after germination, half of the seedlings were transferred into nutrient solution containing 75 mM NaCl, supplemented with 0.24 mM $CaCl_2$. So as not to shock the plants, salt application was made in three 12 hr applications of 25 NaCl and 0.8 mM $CaCl_2$. The plants were allowed to grow for a further 2 weeks before being harvested. The $4^{th}$ fully expanded leaf was removed from each plant, its fresh weight recorded and then incubated at 65° C. for 48 hrs to obtain dried tissue for dry weight measurements. Once weight measurements were obtained the tissue was digested for in 1% nitric acid for 6 hrs at 85° C. $Na^+$ and $K^+$ measurements for each leaf were determined by flame photometry. In addition to the $4^{th}$ leaf, the remaining shoot material from each plant was frozen in liquid nitrogen and RNA extracted to determine the expression levels of AtCIPK16 in transgenic and wild type rice. RNA extract, DNA removal, reverse transcription and PCR were carried out as previously described.

EXAMPLE 22

Constitutive Over-Expression of AtCIPK16 in *Arabidopsis* Decreases the Amount of Shoot $Na^+$ and Increases Salt Tolerance

*Arabidopsis*, ecotype Col-0, was transformed with a 35S: AtCIPK16 construct designed for the constitutive expression of the AtCIPK16 gene, DNA was extracted from $T_1$ transgenic *Arabidopsis* plants transformed with 35S::AtCIPK16 and a Southern blot used to determine the insert number of the transgene. A probe designed to recognise the double CaMV35S promoter driving the expression of the AtCIPK16 transgene was used to probe the DNA. Plant lines 11 and 33, which were used in subsequent experiments, contained two insertions of the transgene.

Figure 8:
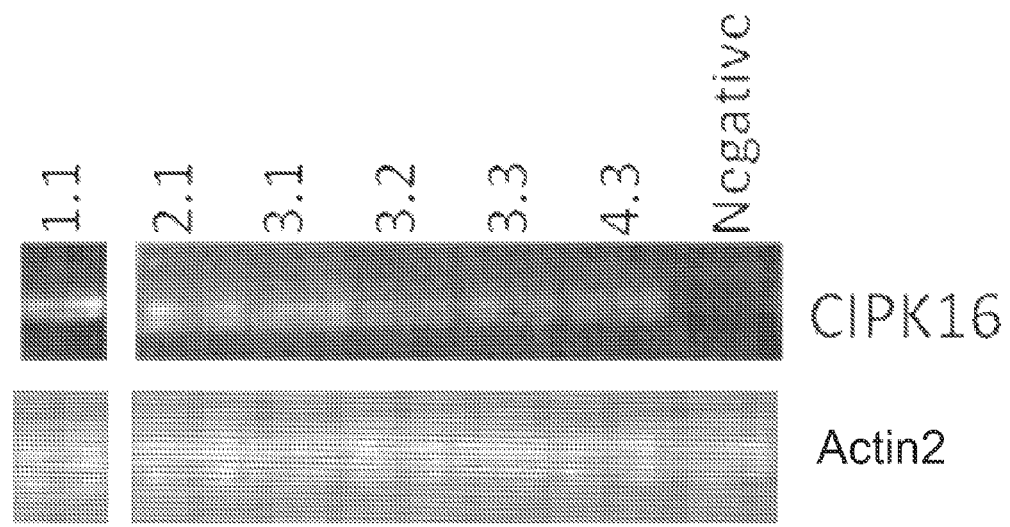
FIG. 8 shows the expression of the AtCIPK16 transgene in $T_1$ *Arabidopsis* plants. RNA was extracted from the shoot of plants growing in soil and cDNA produced. A PCR was used to confirm the presence of the AtCIPK16 and Actin2 genes.

To confirm the expression of the AtCIPK16 transgene in the $T_1$ plants, RNA was extracted from the shoot of plants growing in soil and cDNA produced. PCR was used to confirm the presence of the AtCIPK16 and Actin2 genes. Shoot material was used as it has been previously shown that wild type Col-0 has little to no expression of AtCIPK16 in the shoot under control conditions. As shown in FIG. 8, Lane 1.1 shows the expression of AtCIPK16 in the shoot of Line 11, lane 3.3 shows the expression of the gene in Line 33. The negative lane contains cDNA extracted from wild type Col-0 plants and shows that while the control gene AtACT2 can be amplified from these samples no expression of AtCIPK16 could be observed.

Figure 9:
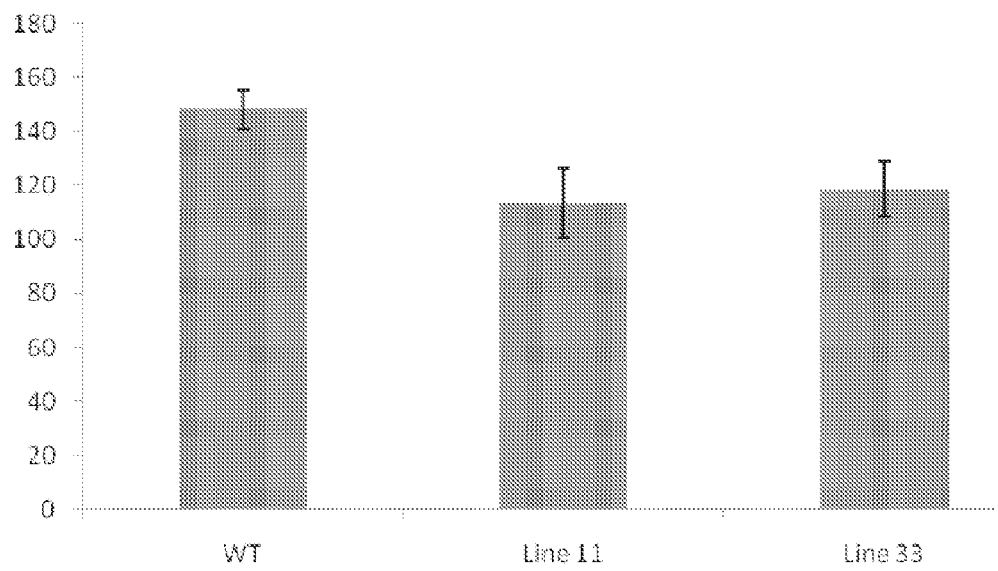
FIG. 9 shows $Na^+$ concentrations, as determined by flame photometry, on average plants from Lines 11, 33 and wild type (WT) Col-0 plants. Results shown are the mean±S.E. of 8-16 biological replicates. Y-axis indicates μmol of $Na^+$/g fresh weight.

Segregating $T_2$ plants from Lines 11 and 33 were grown in hydroponics for 5 weeks before the addition of 100 mM NaCl for 10 days. As shown in FIG. 9, flame photometry determined that, on average, plants from both Lines 11 and 33 have 25% less shoot $Na^+$ than wild type (WT) Col-0 plants. These observations, however, still contain null segregates, which do not over-express the gene. Within this population there were identified a number of individual plants with 30% to 50% the shoot Na$^+$ accumulation and high AtCIPK16 expression.

Figure 10:
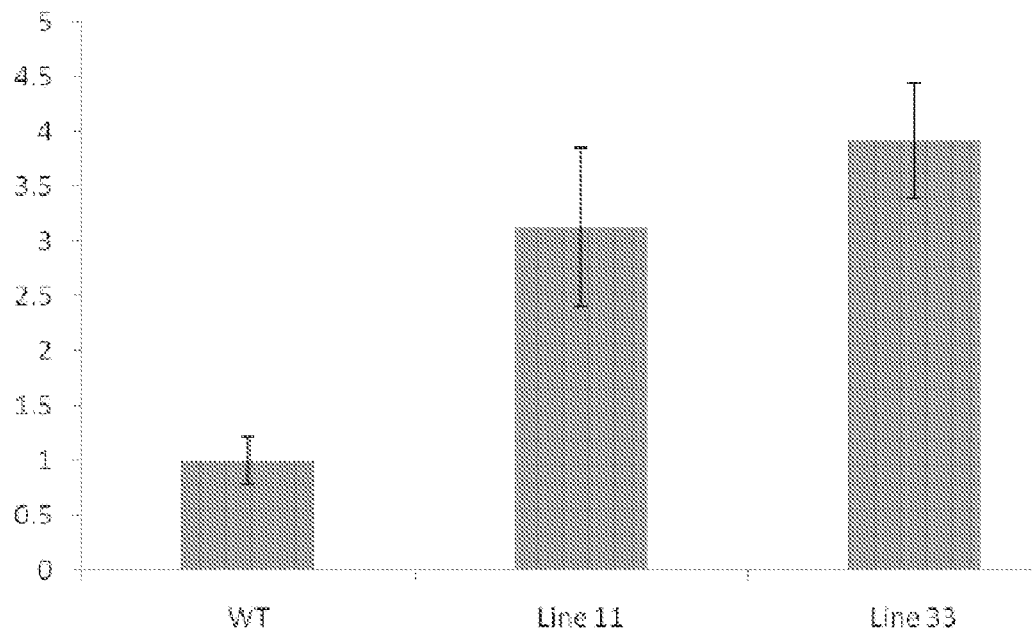
FIG. 10 shows the expression of native AtCIPK16 and AtCIPK16 transgene in the roots of 5 week old *Arabidopsis* plants grown in 100 mM NaCl for 10 days. Results are the mean±S.E. of 8-16 biological replicates. Y-axis indicates relative gene expression, wherein expression level in wild type=1.

RNA was extracted from the roots of 5 week old plants grown in 100 mM NaCl for 10 days and the expression levels of the native AtCIPK16 and AtCIPK16 transgene were determined. As shown in FIG. 10, on average, there was 3 to 4 fold higher expression of AtCIPK16 in the roots of the segregating overexpressing T$_2$ plants of Line 11 and 33 compared to wild type (WT) Col-0.

Figure 11:
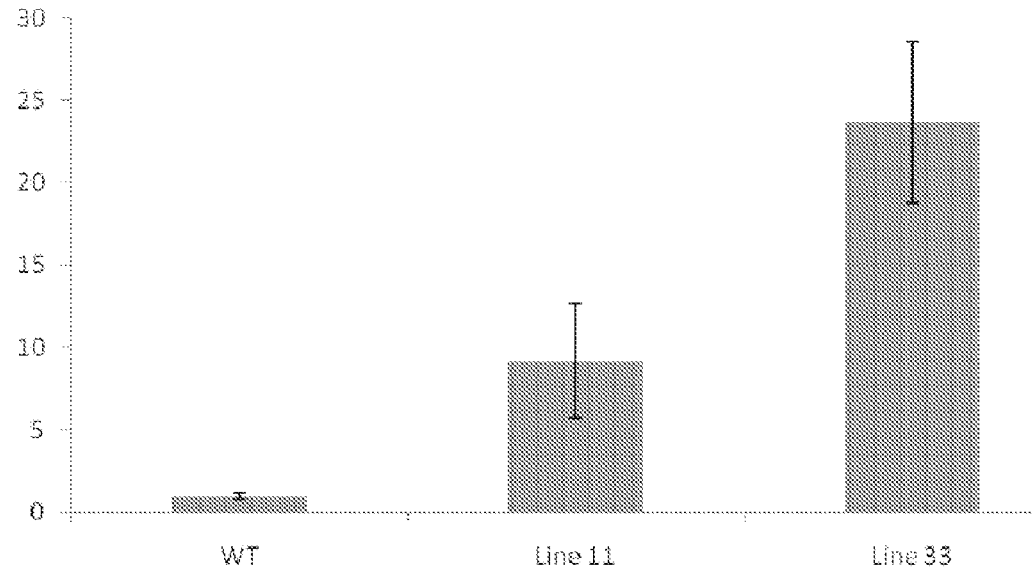
FIG. 11 shows the expression of native AtCIPK16 and AtCIPK16 transgene in the shoots of 5 week old *Arabidopsis* plants grown in 100 mM NaCl for 10 days. Results are the mean±S.E. of 8-16 biological replicates. Y-axis indicates relative gene expression, wherein expression level in wild type=1.

RNA was also extracted from the shoots of 5 week old plants grown in 100 mM NaCl for 10 days and the expression levels of the native AtCIPK16 and transgene were determined. As shown in FIG. 11, on average, there was 10 to 25 fold higher expression of AtCIPK16 in the shoots of the segregating T$_2$ plants of Line 11 and 33 compared to wild type (WT) Col-0. This higher relative expression observed in the shoot compared to roots (FIG. 10) is due to the low shoot expression of AtCIPK16 in wild type Col-0.

Figure 12:
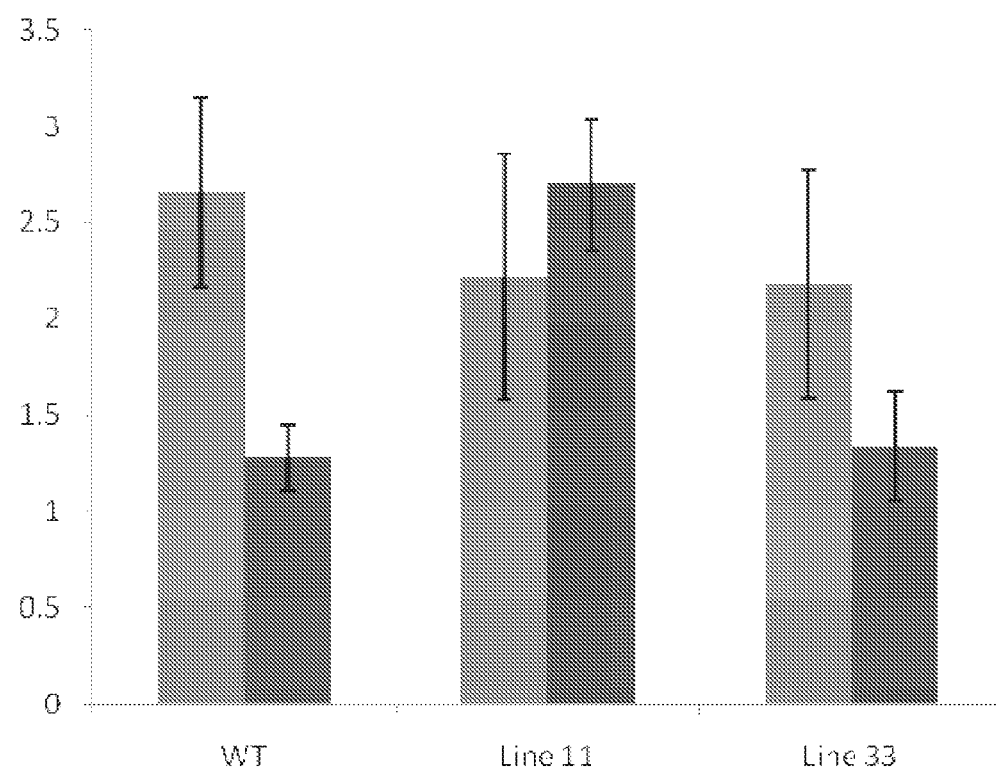
FIG. 12 shows total shoot biomass in $T_2$ segregating *Arabidopsis* plants from Line 11 and 33 as well as wild type (WT) Col-0 plants after 5 weeks growth in hydroponics, followed by the addition of either 0 or 100 mM NaCl for 10 days. Results are the mean±S.E. of 8-16 biological replicates. Y-axis shows fresh weight shoot biomass (g). For each treatment, the left bar indicates fresh weight shoot biomass at 0 mM NaCl, while the right bar is at 100 mM NaCl.

Total shoot biomass was determined in T$_2$ segregating plants from Line 11 and 33 as well as wild type (WT) Col-0 plants after 5 weeks growth in hydroponics, followed by the addition of either 0 or 100 mM NaCl for 10 days. As shown in FIG. 12, while wild type shoot fresh weight was decreased by 50% after 10 days growth in 100 mM NaCl, plants from Line 11 showed no shoot biomass reduction. Although T$_2$ segregating plants from line 33 showed similar reductions in shoot biomass to wild type plants, there were individuals with similar biomass to those observed in Line 11.

EXAMPLE 23

Reduction in the Expression Level of AtCIPK16 Using amiRNA Results in an Increase in the Shoot Na$^+$ Concentration

*Arabidopsis*, ecotype Col-0, was transformed with two separate amiRNA constructs designed to knockdown the expression of the native AtCIPK16 gene. DNA was extracted from T$_1$ transgenic *Arabidopsis* plants transformed with amiRNA AtCIPK16 constructs and a Southern blot used to determine the insert number of the transgene. A probe designed to recognise the double CaMV35S promoter driving the expression of the amiRNA construct was used to probe the DNA. Plant lines 111 and 132, were found to contain the amiRNA CIPK16-1 constructs, while plant lines 222 and 2122, were found to contain the amiRNA CIPK16-2 constructs. Progeny from these four lines were used in subsequent experiments. These plants contained one to five insertions of the amiRNA construct.

Figure 13:
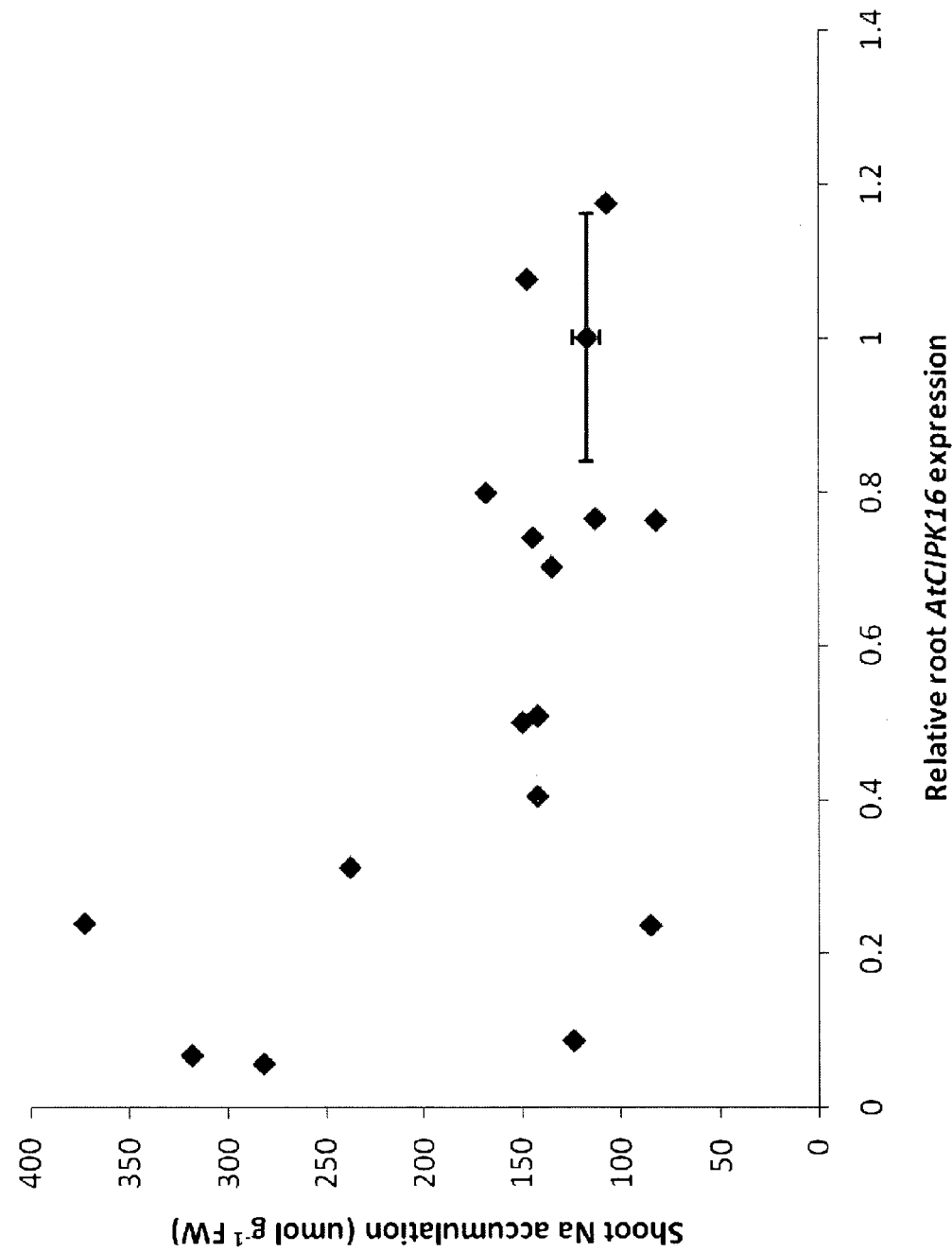
FIG. 13 shows a scatter plot of the results of flame photometry (to determine shoot $Na^+$ accumulation) and semi-quantitative RT-PCR (to estimate levels of AtCIPK26 gene expression) in the *Arabidopsis* amiRNA lines, relative to that of the wild type controls (dot with error bars).

Individual T$_2$ segregating plants from Lines 111, 132, 222 and 2122 were grown in hydroponics for 5 weeks before the addition of 100 mM NaCl for 10 days. Flame photometry was used to determine shoot Na$^+$ accumulation and semi-quantitative RT-PCR used to estimate levels of AtCIPK16 gene expression in the amiRNA lines, relative to that of the wild type controls (shown as dot with error bars in FIG. 13). As shown in FIG. 13, a trend was observed that those amiRNA plants with low root AtCIPK16 expression showed increased shoot Na$^+$ accumulation.

Figure 14:
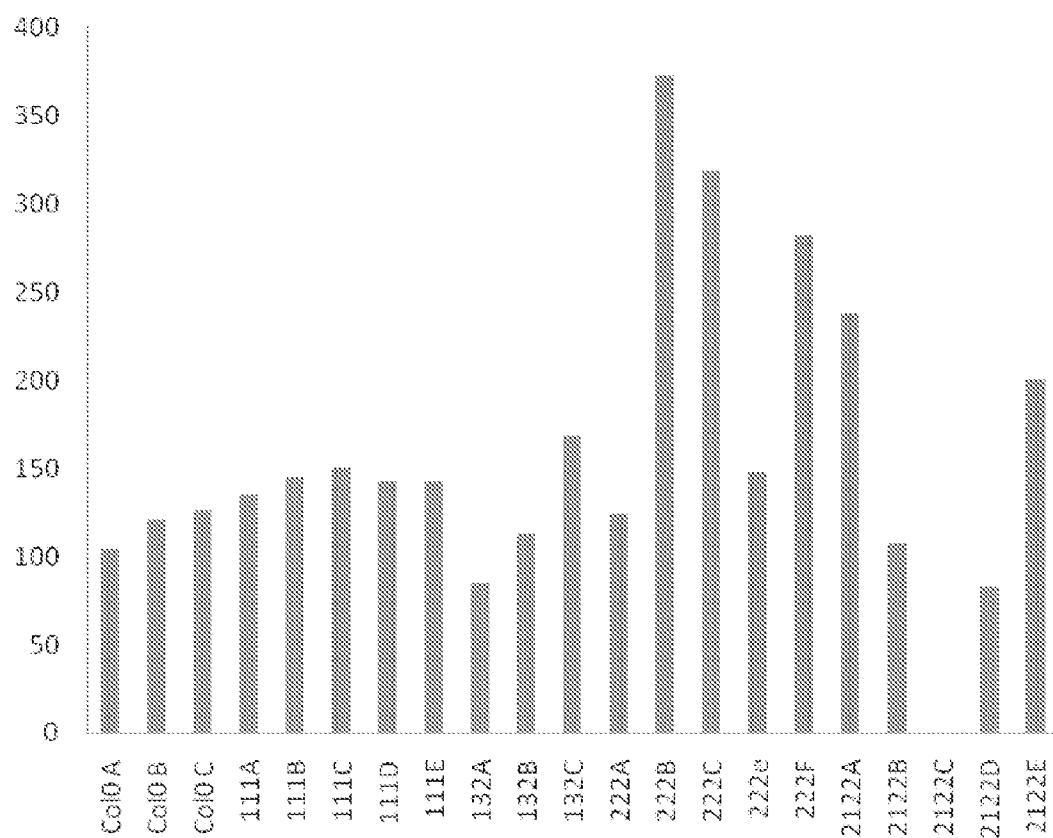
FIG. 14 shows $Na^+$ concentrations, as determined by flame photometry, in individual $T_2$ segregating *Arabidopsis* plants from Lines 111, 132, 222 and 2122 grown in hydroponics for 5 weeks before the addition of 100 mM NaCl for 10 days. Sample 2122C was lost in the extraction. Y-axis indicates μmol of $Na^+$/g fresh weight.

Individual T$_2$ segregating plants from Lines 111, 132, 222 and 2122 were grown in hydroponics for 5 weeks before the addition of 100 mM NaCl for 10 days. As shown in FIG. 14, flame photometry identified a trend for the amiRNA-expressing plants to have higher shoot Na$^+$ than wild type plants.

Figure 15:
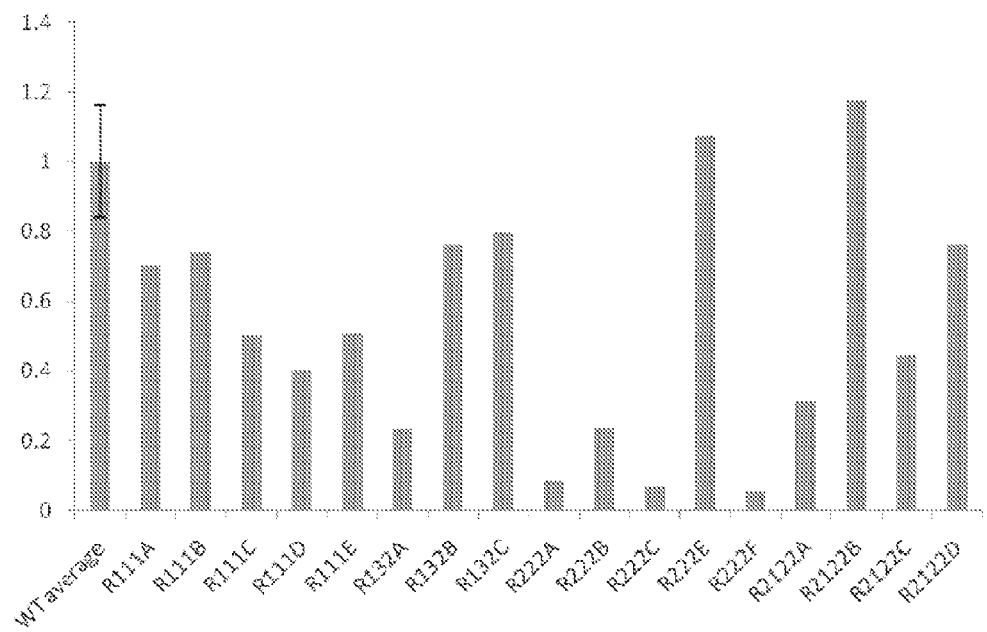
FIG. 15 shows the results of semi-quantitative RT-PCR for AtCIPK16 in individual *Arabidopsis* plants expressing either the amiRNA CIPK16-1 (plants from Line 111 or 132) or amiRNA AtCIPK16-2 (Lines 222 or 2122) when grown in hydroponics for 5 weeks before the addition of 100 mM NaCl for 10 days. Results for wild type (WT) Col-0 plants are the mean±S.E. of 3 biological replicates. Y-axis indicates relative gene expression, wherein expression level in wild type=1.

Individual T$_2$ segregating plants from Lines 111, 132, 222 and 2122 were grown in hydroponics for 5 weeks before the addition of 100 mM NaCl for 10 days. Semi-quantitative RT-PCR determined expression levels of AtCIPK16 in individual plants expressing either the amiRNA CIPK16-1 (plants from Line 111 or 132) or amiRNA AtCIPK16-2 (Lines 222 or 2122). As shown in FIG. 15, many plants showed reduced expression of AtCIPK16 expression in the root and this was related to the amount of Na$^+$ observed in the shoot.

EXAMPLE 24

Over Expression of AtCIPK16 in Rice

Figure 16:
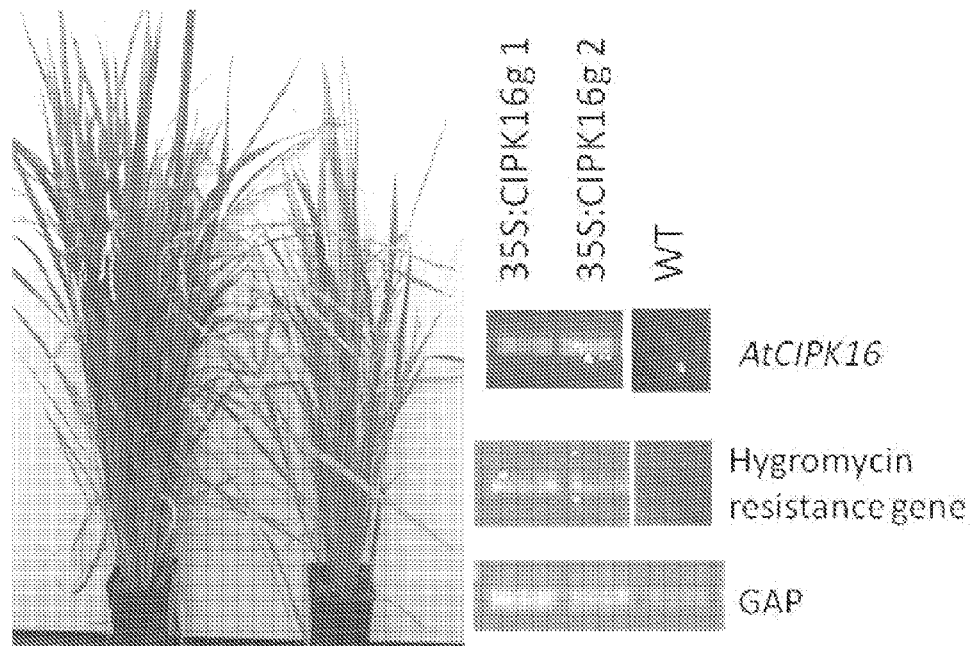
FIG. 16 shows two rice transformants (16-1 and 16-2) (left panel). The right panel shows that both AtCIPK16 and the hygromycin resistance gene could be detected in both 16-1 and 16-2.

Rice callus was transformed with a 35S:AtCIPK16 vector designed to express AtCIPK16 in rice. As shown in FIG. 16, the left panel shows two transformants (16_1 and 16_2), while the right panel shows that both AtCIPK16 and the hygromycin resistance gene (used to select transgenic callus from non-transformed callus) could be detected in both 16-1 and 16-2. The expression of neither gene could be detected in wild type (WI) Nipponbare rice. The expression of the control gene GAP could be detected in all plants.

Figure 17:
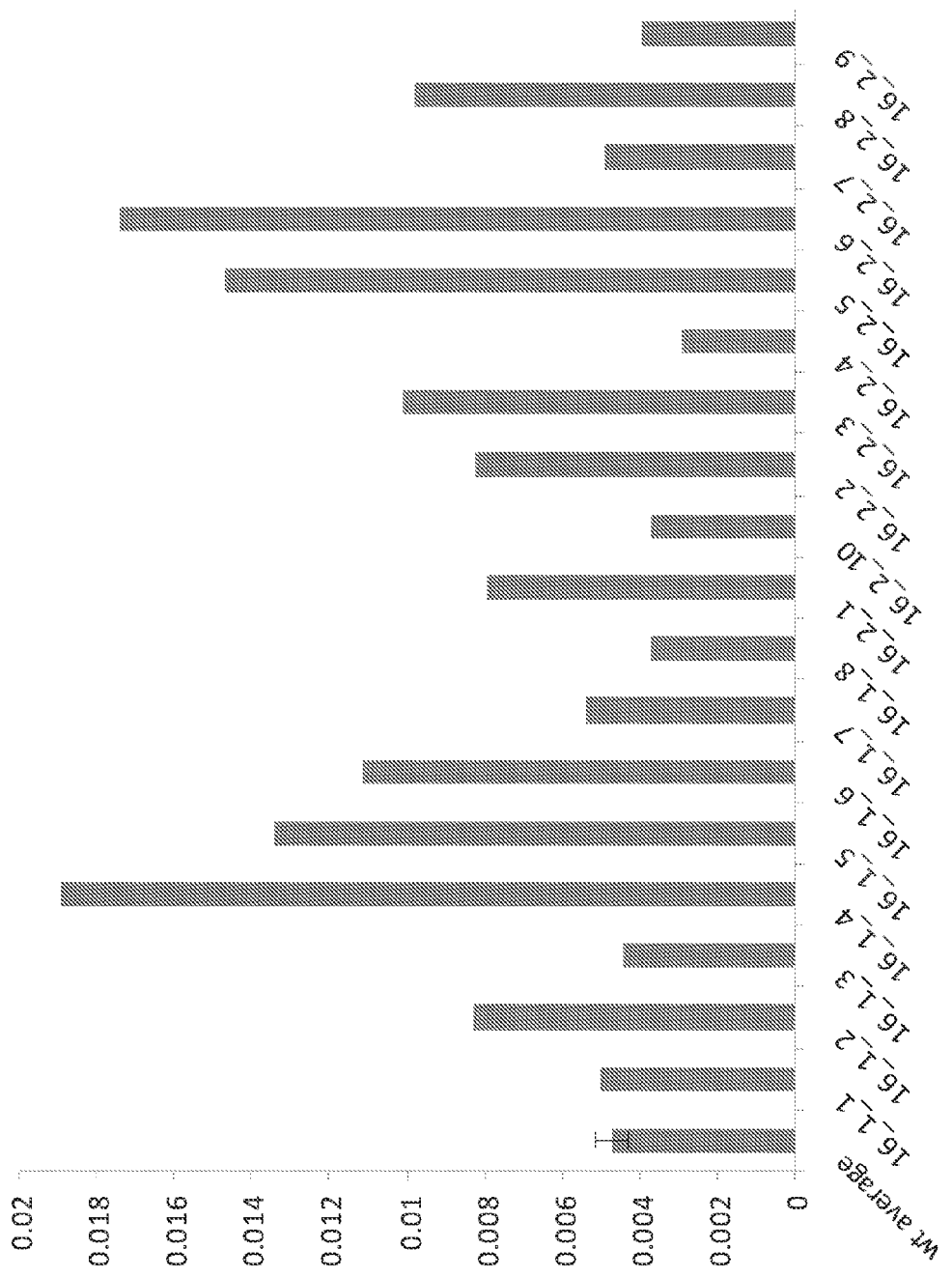
FIG. 17 shows the fourth leaf biomass of segregating $T_2$ 35S::AtCIPK16 rice plants from Lines 16_1 and 16_2 grown in hydroponics for 2 weeks before the addition of 75 mM NaCl for 5 days. Y-axis shows the $4^{th}$ leaf dry weight biomass in g.

Segregating T$_2$ 35S::AtCIPK16 rice plants from Lines 16_1 and 16_2 were grown in hydroponics for 2 weeks before the addition of 75 mM NaCl for 5 days. The fourth leaf of every plant was removed and its dry weight recorded before the concentration of leaf Na$^+$ could be determined. As shown in FIG. 17, there were multiple individual plants with significantly higher leaf biomass when compared to wild type (WT) Nipponbare plants.

Figure 18:
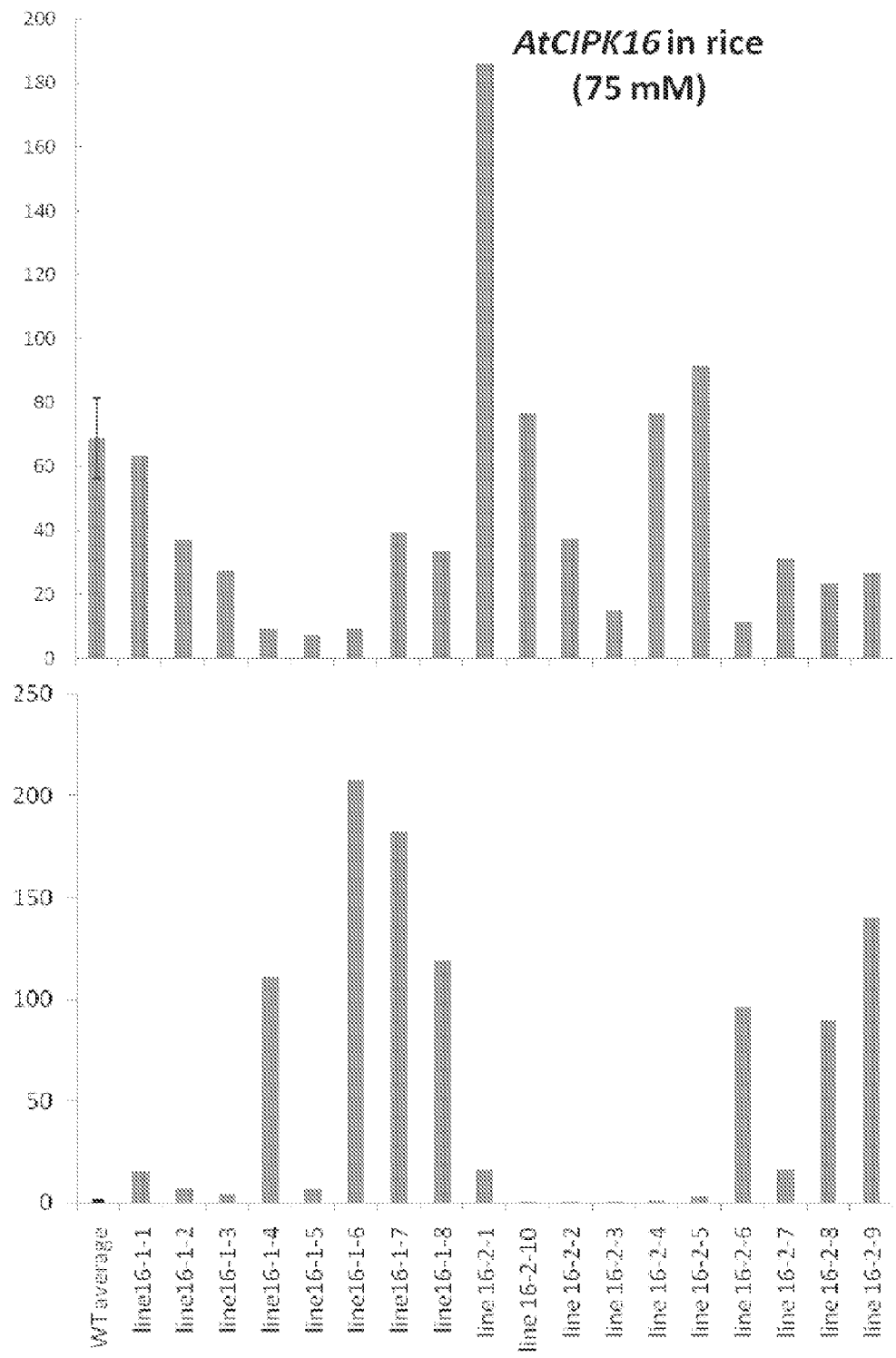
FIG. 18 shows a comparison of shoot sodium concentration (upper) and AtCIPK16 expression (lower) in segregating $T_2$ 35S::AtCIPK16 rice plants from Lines 16_1 and 16_2 grown in hydroponics for 2 weeks before the addition of 75 mM NaCl for 5 days. Y-axis on upper panel indicates μmol $Na^+$/g dry weight. Y-axis on lower panel indicates relative gene expression, wherein expression level in wild type=1.

Segregating T$_2$ 35S::AtCIPK16 rice plants from Lines 16_1 and 16_2 were grown in hydroponics for 2 weeks before the addition of 75 mM NaCl for 5 days. As shown in FIG. 18, plants from both lines with detectable levels of AtCIPK16 expression have significantly lower shoot Na$^+$ than wild type (WT) Nipponbare plants (n=for WI plants). T$_2$ plants from lines 16_1 and 16_2 which did not show expression of the transgene had similar or higher shoot Na$^+$ to wild type plants. Only 4 individual plants did not fit this pattern. Promisingly, plants 16_1_4, 16_1_5, 16_1_6 and 16_2_6 have high expression levels of AtCIPK16 and extremely low shoot Na$^+$.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The claims defining the invention are as follows:

1. A method for modulating the salinity tolerance of a plant cell the method comprising:
   modulating the expression of a CIPK16 polypeptide in the plant cell by introducing into said plant cell a construct comprising a sequence encoding SEQ ID NO: 34 operably linked to a promoter or by introducing into said plant cell an antisense construct comprising a sequence directed against a gene encoding SEQ ID NO: 34;
   applying a salinity stress to the plant cell; and
   comparing expression of the CIPK16 polypeptide in the plant cell with expression of the CIPK16 polypeptide in a wild-type form of the plant cell under the salinity stress; wherein modulated expression of the CIPK16 polypeptide in the plant cell compared to the expression of the CIPK16 polypeptide in the wild-type form of the plant cell identifies the plant cell as a plant cell with modulated salinity tolerance,
   thereby confirming modulation of the salinity tolerance of the plant cell.

2. The method of claim 1, wherein expression of the CIPK16 polypeptide is upregulated in the plant cell and the salinity tolerance of the plant cell is increased relative to a wild-type form of the plant cell.

3. The method of claim 1, wherein expression of the CIPK16 polypeptide is downregulated in the plant cell and the salinity tolerance of the plant cell is decreased relative to a wild-type form of the plant cell.

4. A method for modulating the salinity tolerance of a multicellular structure comprising a plurality of plant cells, the method comprising:
   modulating the expression of a CIPK16 polypeptide in one or more of the plant cells of the multicellular structure by introducing into said one or more plant cells a construct comprising a sequence encoding SEQ ID NO: 34 operably linked to a promoter or by introducing into said one or more plant cells an antisense construct comprising a sequence directed against a gene encoding SEQ ID NO: 34;
   applying a salinity stress to the one or more plant cells; and
   comparing expression of the CIPK16 polypeptide in the one or more plant cells of the multicellular structure with expression of the CIPK16 polypeptide in a wild-type form of the one or more plant cells in a multicellular structure under the same salinity stress;
   wherein modulated expression of the CIPK16 polypeptide in the one or more plant cells compared to the expression of the CIPK16 polypeptide in the wild-type form of the one or more plant cells in a multicellular structure identifies the multicellular structure as a multicellular structure with modulated salinity tolerance,
   thereby confirming modulation of the salinity tolerance of the multicellular structure.

5. The method of claim 4 wherein expression of a CIPK16 polypeptide is upregulated in the one or more plant cells and the salinity tolerance of the multicellular structure is increased relative to a wild-type form of the multicellular structure.

6. The method of claim 4 wherein expression of a CIPK16 polypeptide is downregulated in the one or more plant cells and the salinity tolerance of the multicellular structure is decreased relative to a wild-type form of the multicellular structure.

7. The method of claim 4, wherein the multicellular structure comprises a whole plant, plant tissue, plant organ, plant part, plant reproductive material or cultured plant tissue.

8. The method of claim 7, wherein the multicellular structure comprises a plant or a part thereof and modulation of the salinity tolerance of the plant or part thereof is effected by modulating the expression of a CIPK16 polypeptide in at least one or more root cells of the plant or a part thereof.

* * * * *

SEQUENCE LISTING

<160> NUMBER OF SEQ ID NOS: 34

<210> SEQ ID NO 1
<211> LENGTH: 1981
<212> TYPE: DNA
<213> ORGANISM: Arabidopsis thaliana
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t

<400> SEQUENCE: 1

```
tttatcaaca acaccaatta ttattttatt ttctcnggtt caagaaattg tctaagctcc      60
attcaaacat tctgtactta tatataaagt ttacatcatc acatattgtg catcaaatag     120
caaaggtttt ggcaacatac atataatatg aatcgtgctt gtccncacac acacacatgt     180
atatatatgt ntttattgtt tacccttgaa caacnttttt nggtaagggg gtcttctatc     240
atcaggaaaa cataaggnag atgaggtaac atctttagat tcgttcgaag tagaactcct     300
atgcatttga tcaanttgtt ttctaattaa gtaatgcaac atttaaacca tgtgcagcac     360
aaacgatggc ttatttaggt ggatttgcaa atcttttcac tctttagggc atattccaat     420
caactactgc ttgaaatttg actgatcaat gtgatgcaaa attcacggca tggcttgttt     480
tagcagctag tttcgacaac ctaatcaccc gaaaataaca aacaatcgga aatgcagcgc     540
gataagtaga tatatgtctg tgatcaccca attagccaca aaatagtgta ctatgtttgt     600
gatgttaccc ttttactctt caattttaaa tacatatctc gttatagtat ttttttttt      660 tttttttttt ttttttttgg gtaaaactcg ttatagtatt tcgttagagt attaacattt     720
gtgtaaacat aattgttgtc attaatcgtg ggtccaaatc atgacacatc acaaagtttc     780
ttggacttgt tatacatgtt ccttaaaatg attagttata tattatctta ataatcctga     840
tctttaaatc gaacaaattt agatttagct tcttcttttt ttgttaaaat ttagatttag     900
ctttacaaga tgtacctttg attatgatag aggaaaataa cagtatccca cccaaataca     960
cggttataat gagattttca tgtatgtaga aaaatcatca aattgtaaga aaacaattgg    1020
aaaaattgag tgtgttgttt tgagtagcaa atatgaaga atccatcaaa ccaagaaatt    1080
agcaaagatg tagaaaggaa gatttggtcg atagattcac ggacgtatta gaatgccca    1140 cttccgata caatcgtccc aactaggaaa agactcaaag cttttcgaaa gaaatgaaa    1200 aatcctctat gaaaaataag tcaagaaatt gttttaaaaa tatttaaggg ccaagtagaa    1260
```

-continued

```
aaggtcacat cttgccttac caaaaaaaga cagttcattg aaattttatc gggacaagtt    1320
tactattttt aattaatgcg tatctacttc aaaacatgcg tagcattaac ggcgattcca    1380
cgtcaatttc atggcgtcca caattttgt  ataaggataa gagagttact tttatatttt    1440
taaaatctat tctgaaaact ttaagaactt atttacatga atacatggtc agaaatgtgc    1500
gagaccattg tttaactggt taaaaaagga tttatttaca tagaaatgga tttaaatcac    1560
ctgttacact tttattgaaa tcattctctt atgatcattg catcgtaact cgagatattt    1620 attttcatg  ctttagtttg ttaattatat ctagttttat catgttctat aacccttttt    1680
taggcactca acataaatag caaaccccga tttagttcaa ttcgcgaatc aatttcgtct    1740
tggttattct tttggctttg gtcgtattta attatgctag ctgccagatc ttaggcacat    1800
cactttgttt agataagatt agaacatttc ttcacagttc acttagtcgt cacatatcaa    1860
acaaagtaga taacattata aataaaaaaa ttccacaaat aatttctgct tatatataac    1920
caaatcacaa atttccacat aattagtctc acatatactt gtaactagtc agacaaagac    1980
a                                                                    1981

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2
tgatgtgatg aattggaagg cg                                               22

<210> SEQ ID NO 3
<211> LENGTH: 22
<212> TYPE: DNA
<213> ORGANISM: Artificial
<220> FEATURE:
<223> OTHER INFORMATION: primer

<400> SEQUENCE: 3
actctcaaga ttgcttgtgc cg                                               22

<210> SEQ ID NO 4
<211> LENGTH: 23
<212> TYPE: DNA
<213> ORGANISM: Artificial
<220> FEATURE:
<223> OTHER INFORMATION: primer

<400> SEQUENCE: 4
tggcgaacgc tggtcctaat aca                                              23

<210> SEQ ID NO 5
<211> LENGTH: 24
<212> TYPE: DNA
<213> ORGANISM: Artificial
<220> FEATURE:
<223> OTHER INFORMATION: primer

<400> SEQUENCE: 5
caaaaactcc tctgccccaa tcaa                                             24

<210> SEQ ID NO 6
<211> LENGTH: 20
<212> TYPE: DNA
```

```
<213> ORGANISM: Artificial
<220> FEATURE:
<223> OTHER INFORMATION: primer

<400> SEQUENCE: 6
atgtgggtca gggtatggaa                                              20

<210> SEQ ID NO 7
<211> LENGTH: 24
<212> TYPE: DNA
<213> ORGANISM: Artificial
<220> FEATURE:
<223> OTHER INFORMATION: primer

<400> SEQUENCE: 7
ccgacaacct tcttagtctc ctct                                         24

<210> SEQ ID NO 8
<211> LENGTH: 25
<212> TYPE: DNA
<213> ORGANISM: Artificial
<220> FEATURE:
<223> OTHER INFORMATION: primer

<400> SEQUENCE: 8
tggttgatct cgttgtgcag gtctc                                        25

<210> SEQ ID NO 9
<211> LENGTH: 24
<212> TYPE: DNA
<213> ORGANISM: Artificial
<220> FEATURE:
<223> OTHER INFORMATION: primer

<400> SEQUENCE: 9
gtcagccaag tcaacaactc tctg                                         24

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
atggaagaat caaaccgtag tagtactgtc                                   30

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
ttggaattgg atgtgcgagg                                              20

<210> SEQ ID NO 12
<211> LENGTH: 21
<212> TYPE: DNA
<213> ORGANISM: Artificial
<220> FEATURE:
<223> OTHER INFORMATION: amiRNA AtCIPK16-1

<400> SEQUENCE: 12
ttttcgtcga taaacggcaa g                                            21
```

<210> SEQ ID NO 13
<211> LENGTH: 21
<212> TYPE: DNA
<213> ORGANISM: Artificial
<220> FEATURE:
<223> OTHER INFORMATION: amiRNA AtCIPK16-2

<400> SEQUENCE: 13
ttattccgta aaacctccgg c                                              21

<210> SEQ ID NO 14
<211> LENGTH: 40
<212> TYPE: DNA
<213> ORGANISM: Artificial
<220> FEATURE:
<223> OTHER INFORMATION: primer

<400> SEQUENCE: 14
gattttcgtc gataaacggc aggtctctct tttgtattcc                          40

<210> SEQ ID NO 15
<211> LENGTH: 40
<212> TYPE: DNA
<213> ORGANISM: Artificial
<220> FEATURE:
<223> OTHER INFORMATION: primer

<400> SEQUENCE: 15
gacctgccgt ttatcgacga aaatcaaaga gaatcaatga                          40

<210> SEQ ID NO 16
<211> LENGTH: 40
<212> TYPE: DNA
<213> ORGANISM: Artificial
<220> FEATURE:
<223> OTHER INFORMATION: primer

<400> SEQUENCE: 16
gacccgccgt ttatccacga aattcacagg tcgtgatatg                          40

<210> SEQ ID NO 17
<211> LENGTH: 40
<212> TYPE: DNA
<213> ORGANISM: Artificial
<220> FEATURE:
<223> OTHER INFORMATION: primer

<400> SEQUENCE: 17
gaatattccc taaaacctcc tgctctacat atatattcct                          40

<210> SEQ ID NO 18
<211> LENGTH: 39
<212> TYPE: DNA
<213> ORGANISM: Artificial
<220> FEATURE:
<223> OTHER INFORMATION: primer

<400> SEQUENCE: 18
gattattccg taaaacctcc cgctctctct tttgtattc                           39

<210> SEQ ID NO 19
<211> LENGTH: 40
<212> TYPE: DNA
<213> ORGANISM: Artificial
<220> FEATURE:

```
<223> OTHER INFORMATION: primer

<400> SEQUENCE: 19
gagcgggagg ttttacggaa taatcaaaga gaatcaatga                          40

<210> SEQ ID NO 20
<211> LENGTH: 39
<212> TYPE: DNA
<213> ORGANISM: Artificial
<220> FEATURE:
<223> OTHER INFORMATION: primer

<400> SEQUENCE: 20
gagcaggagg tttttagggat attcacaggt cgtgatatg                          39

<210> SEQ ID NO 21
<211> LENGTH: 40
<212> TYPE: DNA
<213> ORGANISM: Artificial
<220> FEATURE:
<223> OTHER INFORMATION: primer

<400> SEQUENCE: 21
gaatattccc taaaacctcc tgctctacat atatattcct                          40

<210> SEQ ID NO 22
<211> LENGTH: 25
<212> TYPE: DNA
<213> ORGANISM: Artificial
<220> FEATURE:
<223> OTHER INFORMATION: primer

<400> SEQUENCE: 22
ctgcaaggcg attaagttgg gtaac                                          25

<210> SEQ ID NO 23
<211> LENGTH: 27
<212> TYPE: DNA
<213> ORGANISM: Artificial
<220> FEATURE:
<223> OTHER INFORMATION: primer

<400> SEQUENCE: 23
gcggataaca atttcacaca ggaaaca                                        27

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
cattgatgat gccagaaggg c                                              21

<210> SEQ ID NO 25
<211> LENGTH: 22
<212> TYPE: DNA
<213> ORGANISM: Artificial
<220> FEATURE:
<223> OTHER INFORMATION: primer

<400> SEQUENCE: 25
aattctttgt tcaggatccg gc                                             22
```

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
gatgttggcg acctcgtatt                                               20

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
gtgcttgaca ttggggagtt                                               20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
gaagtccagc tgccagaaac                                               20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
aagcacggtc aacttccgta                                               20

<210> SEQ ID NO 30
<211> LENGTH: 22
<212> TYPE: DNA
<213> ORGANISM: Artificial
<220> FEATURE:
<223> OTHER INFORMATION: primer

<400> SEQUENCE: 30
ttgtgtgtga caaactctct gg                                            22

<210> SEQ ID NO 31
<211> LENGTH: 21
<212> TYPE: DNA
<213> ORGANISM: Artificial
<220> FEATURE:
<223> OTHER INFORMATION: primer

<400> SEQUENCE: 31
ggcatcaatt cgatcactca g                                             21

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
gggctgctag cttcaacatc                                          20

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
ttgattgcag ccttgatctg                                          20

<210> SEQ ID NO 34
<211> LENGTH: 469
<212> TYPE: PRT
<213> ORGANISM: Arabidopsis thaliana

<400> SEQUENCE: 34

Met Glu Glu Ser Asn Arg Ser Ser Thr Val Leu Phe Asp Lys Tyr Asn
1               5                   10                  15

Ile Gly Arg Leu Leu Gly Thr Gly Asn Phe Ala Lys Val Tyr His Gly
            20                  25                  30

Thr Glu Ile Ser Thr Gly Asp Asp Val Ala Ile Lys Val Ile Lys Lys
        35                  40                  45

Asp His Val Phe Lys Arg Arg Gly Met Met Glu Gln Ile Glu Arg Glu
    50                  55                  60

Ile Ala Val Met Arg Leu Leu Arg His Pro Asn Val Val Glu Leu Arg
65                  70                  75                  80

Glu Val Met Ala Thr Lys Lys Lys Ile Phe Phe Val Met Glu Tyr Val
                85                  90                  95

Asn Gly Gly Glu Leu Phe Glu Met Ile Asp Arg Asp Gly Lys Leu Pro
            100                 105                 110

Glu Asp Leu Ala Arg Lys Tyr Phe Gln Gln Leu Ile Ser Ala Val Asp
        115                 120                 125

Phe Cys His Ser Arg Gly Val Phe His Arg Asp Ile Lys Pro Glu Asn
    130                 135                 140

Leu Leu Leu Asp Gly Glu Gly Asp Leu Lys Val Thr Asp Phe Gly Leu
145                 150                 155                 160

Ser Ala Leu Met Met Pro Glu Gly Leu Gly Arg Arg Gly Ser Ser
                165                 170                 175

Asp Asp Leu Leu His Thr Arg Cys Gly Thr Pro Ala Tyr Val Ala Pro
            180                 185                 190

Glu Val Leu Arg Asn Lys Gly Tyr Asp Gly Ala Met Ala Asp Ile Trp
        195                 200                 205

Ser Cys Gly Ile Val Leu Tyr Ala Leu Leu Ala Gly Phe Leu Pro Phe
    210                 215                 220

Ile Asp Glu Asn Val Met Thr Leu Tyr Thr Lys Ile Phe Lys Ala Glu
225                 230                 235                 240

Cys Glu Phe Pro Pro Trp Phe Ser Leu Glu Ser Lys Glu Leu Leu Ser
                245                 250                 255

Arg Leu Leu Val Pro Asp Pro Glu Gln Arg Ile Ser Met Ser Glu Ile
            260                 265                 270

Lys Met Ile Pro Trp Phe Arg Lys Asn Phe Thr Pro Ser Val Ala Phe
        275                 280                 285

Ser Ile Asp Glu Thr Ile Pro Ser Pro Pro Glu Pro Thr Lys Lys

-continued

```
            290                 295                 300
Lys Lys Lys Asp Leu Asn Glu Lys Glu Asp Asp Gly Ala Ser Pro Arg
305                 310                 315                 320

Ser Phe Asn Ala Phe Gln Phe Ile Thr Ser Met Ser Ser Gly Phe Asp
                325                 330                 335

Leu Ser Asn Leu Phe Glu Ile Lys Arg Lys Pro Lys Arg Met Phe Thr
                340                 345                 350

Ser Lys Phe Pro Ala Lys Ser Val Lys Glu Arg Leu Glu Thr Ala Ala
                355                 360                 365

Arg Glu Met Asp Met Arg Val Lys His Val Lys Asp Cys Lys Met Lys
                370                 375                 380

Leu Gln Arg Arg Thr Glu Gly Arg Lys Gly Arg Leu Ser Val Thr Ala
385                 390                 395                 400

Glu Val Phe Glu Val Ala Pro Glu Val Ser Val Val Glu Phe Cys Lys
                405                 410                 415

Thr Ser Gly Asp Thr Leu Glu Tyr Tyr Leu Phe Cys Glu Asp Asp Val
                420                 425                 430

Arg Pro Ala Leu Lys Asp Ile Val Trp Ser Trp Gln Gly Asp Asp Asp
                435                 440                 445

Glu Asp Asp Val Thr Thr Asn Asp Asn Val Asp Thr Asn Asp Asn Lys
                450                 455                 460

Ile Asn Asn Val Ser
465
```